United States Patent [19]
Commons et al.

[11] Patent Number: 5,952,354
[45] Date of Patent: Sep. 14, 1999

[54] TRIS CARBAMIC ACID ESTERS: INHIBITORS OF CHOLESTEROL ABSORPTION

[75] Inventors: Thomas Joseph Commons, Wayne; Donald Peter Strike, St. Davids; Christa Marie LaClair, Newtown, all of Pa.

[73] Assignee: American Home Products Corporation, Madison, N.J.

[21] Appl. No.: 08/095,140

[22] Filed: Jul. 21, 1993

[51] Int. Cl.$^6$ .................. A61K 31/445; C07D 211/36
[52] U.S. Cl. .................. 514/327; 514/210; 514/211; 514/212; 514/227.5; 514/227.8; 514/228.2; 514/231.2; 514/237.8; 514/255; 514/256; 514/269; 514/278; 514/307; 514/309; 514/311; 514/312; 514/313; 514/316; 514/317; 514/318; 514/319; 514/320; 514/321; 514/322; 514/323; 514/328; 514/330; 514/365; 514/366; 514/367; 514/372; 514/373; 514/374; 514/375; 514/378; 514/379; 514/396; 514/397; 514/398; 540/466; 540/480; 540/481; 540/482; 540/543; 540/604; 544/59; 544/60; 544/61; 544/62; 544/111; 544/298; 544/315; 544/316; 544/319; 544/405; 546/16; 546/141; 546/153; 546/157; 546/186; 546/187; 546/188; 546/208; 546/209; 546/210; 546/212; 546/214; 548/146; 548/152; 548/182; 548/206; 548/215; 548/225; 548/240; 548/241; 548/243; 548/262.4; 548/264.2; 548/264.1; 548/950; 548/952
[58] Field of Search .................. 546/222, 16; 514/327, 514/278

[56] References Cited

U.S. PATENT DOCUMENTS

| 5,112,859 | 5/1992 | Commons et al. .................. 514/484 |
| 5,169,844 | 12/1992 | Commons et al. .................. 514/211 |

FOREIGN PATENT DOCUMENTS

| 428385 | 5/1991 | European Pat. Off. ...... C07C 211/00 |
| 2612186 | 9/1988 | France .................. C07D 271/06 |
| 3702876 | 8/1988 | Germany .................. C07C 121/60 |
| 56-071058 | 6/1981 | Japan .................. C07C 125/067 |
| 1592011 | 7/1981 | United Kingdom .................. A01N 31/14 |

OTHER PUBLICATIONS

Hoisie, et al., J. Biol. Chem. 262, 260–264 (1987).
De Vries, et al., J. Med. Chem. 29, 1131 (1986).
Gallo, et al., J. LIpid Research 25, 604–612 (1984).
Gallo, et al., Proc. Soc. Exp. Biol. and Med. 156, 277–281 (1977).
Scofield, et al., Biochemistry 16, 22492–2496 (1977).

*Primary Examiner*—Shailendra Kumar
*Attorney, Agent, or Firm*—Michael R. Nagy

[57] ABSTRACT

Inhibition of the enzymes cholesterol ester hydrolase (CEH) and/or acyl coenzyme A: cholesterol acyltransferase (ACAT) results in the inhibition of the esterification of cholesterol and are therefore implicated in the inhibition of absorption of cholesterol and thus can lower serum cholesterol levels. Compounds of the formula:

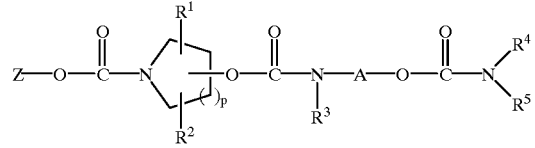

where Z is $$Z \text{ is } —Ar^1, \quad —Ar^1—Ar^2, \quad —Ar^1—O—Ar^2,$$

$$—Ar^1—S—Ar^2, \quad —Ar^1—O—\overset{O}{\underset{\|}{C}}—Ar^2,$$

$$—Ar^1—\overset{O}{\underset{\|}{C}}—O—Ar^2, \quad —Ar^1—\overset{O}{\underset{\|}{C}}—Ar^2,$$

$$—Ar^1—(CH_2)_{1-20}—Ar^2, \quad —Ar^1—(CH_2)_{1-20}—O—Ar^2,$$

$$—Ar^1—O—(CH_2)_{1-20}—Ar^2$$

or $—Ar^1—(CR=CR)_{1-3}—Ar^2$, $—AR^1—NR^7—AR^2$ and A is a linking group inhibit the enzymes CEH and/or ACAT (in vitro) and inhibit absorption of cholesterol.

27 Claims, No Drawings

TRIS CARBAMIC ACID ESTERS: INHIBITORS OF CHOLESTEROL ABSORPTION

BACKGROUND OF THE INVENTION

Cholesterol ester hydrolase and acyl-CoA cholesterol acyltransferase have been implicated in the reesterification and absorption of exogenous cholesterol. It has been demonstrated that removal of CEH from pancreatic juice results in an 80% reduction in the uptake of cholesterol into the bloodstream in rats [Hoisie, J. Biol. Chem. 260–264 (1987).] Furthermore, several lines of investigation have indicated that ACAT may play a key role in the intestinal absorption of cholesterol [DeVries et al., J. Med. Chem. 22, 1131 (1986)]. The association between high serum cholesterol levels and coronary vascular disease is well documented; consequently compounds of this invention may be useful for treating atherosclerosis, familial hypercholesterolemia, hyperlipidemia, and like diseases.

SUMMARY OF THE INVENTION

This invention relates to novel carbamic acid esters of 4 to 8 membered azacycloalkanols, particularly 4-piperidinol, which inhibit absorption of cholesterol from the intestinal tract and have been shown to inhibit the enzymes, cholesterol ester hydrolase (CEH) and/or acyl-CoA cholesterol acyltransferase (ACAT). The novel CEH/ACAT inhibitors of this invention have the formula:

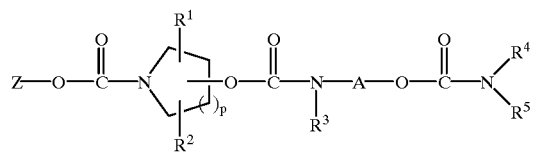

wherein p is 0, 1, 2, 3, or 4;

Z is —$Ar^1$, —$Ar^1$—$Ar^2$, —$Ar^1$—O—$Ar^2$,

—$Ar^1$—S—$Ar^2$, —$Ar^1$—O—$\overset{\overset{O}{\|}}{C}$—$Ar^2$

—$Ar^1$—$\overset{\overset{O}{\|}}{C}$—O—$Ar^2$, —$Ar^1$—$\overset{\overset{O}{\|}}{C}$—$Ar^2$, —$Ar^1$—$(CH_2)_{1-20}$-$Ar^2$, —$Ar^1$—$(CH_2)_{1-20}$—O—$Ar^2$, —$Ar^1$—O—$(CH_2)_{1-20}$—$Ar^2$, —$Ar^1$—$(CR^6=CR^6)_{1-3}$—$Ar^2$ or —$Ar^1$—$NR^7$—$Ar^2$;

where $R^6$ is hydrogen or $C_1$-$C_8$ alkyl and $R^7$ is hydrogen, $C_1$-$C_8$ alkyl, $C_1$-$C_8$ alkylcarbonyl or $C_1$-$C_8$ alkoxycarbonyl;

and $Ar^1$ and $Ar^2$ are, independently, selected from phenyl, naphthyl, furanyl, benzofuranyl, dibenzofuranyl, pyridinyl, pyrimidinyl, pyrazinyl, thienyl, benzothienyl, imidazolyl, oxazolyl, benzoxazolyl, thiazolyl, benzthiazolyl, isoxazolyl, benzisoxazolyl, indenyl, indolyl, quinolinyl, isoquinolinyl, benzotriazolyl, carbazolyl, benzimidazolyl, or fluorenyl;

and $Ar^1$ and $Ar^2$, independently, are optionally substituted by fluorine, chlorine, bromine, iodine, cyano, nitro, —$CO_2H$, $C_1$-$C_{20}$ alkyl, $C_2$-$C_{20}$ alkenyl, $C_3$-$C_8$ cycloalkyl, $C_1$-$C_{20}$ alkoxy, $C_1$-$C_{20}$ alkyl-O—($C_1$-$C_{20}$alkyl)—, $C_1$-$C_{20}$ alkyl-O—($C_1$-$C_{20}$alkyl)—O—, trifluoromethyl, $C_1$-$C_{20}$ alkylcarbonyl, $C_3$-$C_8$ cycloalkyloxy, $C_1$-$C_{20}$ alkylcarbonyloxy, $C_1$-$C_{20}$ alkoxycarbonyl, mono or di $C_1$-$C_{20}$ alkylaminocarbonyl, tetrazolyl, —OH, —$(CH_2)_{1-6}$—OH, —SH, —$NH_2$ or —$(CH_2)_{1-6}$—$NR^8R^9$ where $R^8$ is $C_1$-$C_{20}$ alkyl, $C_1$-$C_{20}$ alkylcarbonyl, $C_1$-$C_{20}$ alkoxycarbonyl and $R^9$ is hydrogen or $C_1$-$C_{20}$ alkyl or $R^8$ and $R^9$ together with the interposed nitrogen atom form a heterocyclic ring of the formula:

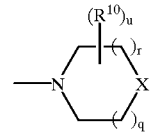

where q is 0, 1 or 2, r is 1 or 2, u is 0, 1 or 2, $R^{10}$ is $C_1$-$C_8$ alkyl and X is —O—, —S—, —$NR^{11}$— where $R^{11}$ is H, $C_1$-$C_{20}$ alkyl or benzyl or —$CR^{12}R^{13}$— where $R^{12}$ is H, OH, $C_1$-$C_{20}$ alkyl, $C_1$-$C_{20}$ alkoxy, $C_1$-$C_{20}$ alkylcarbonyloxy, $Ar^1$ or —$(CH_2)_{1-10}$—$Ar^1$, $R^{13}$ is H, $C_1$-$C_{20}$ alkyl, or $R^{12}$ and $R^{13}$ together with the interposed carbon forms a 3 to 8 membered carbocyclic ring;

A is a bridging group selected from:

a saturated or unsaturated, straight or branched hydrocarbon chain of 1 to 20 carbons and which may have 1 to 6 sites of olefinic and/or acetylenic unsaturation;

a group of the formula:

—$(CH_2)_m$—W—$(CH_2)_n$— where m and n are 1 to 19, m+n is 2 to 20 and W is a group selected from —O—, —S—, or —$NR^{14}$— where $R^{14}$ is hydrogen, $C_1$-$C_{20}$ alkyl, $C_1$-$C_{20}$ alkylcarbonyl, $C_1$-$C_{20}$ alkoxycarbonyl, or benzyl;

a group of the formula:

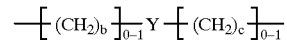

where b and c are 1 to 20, b+c is 1 to 20 and Y is selected from the group consisting of:

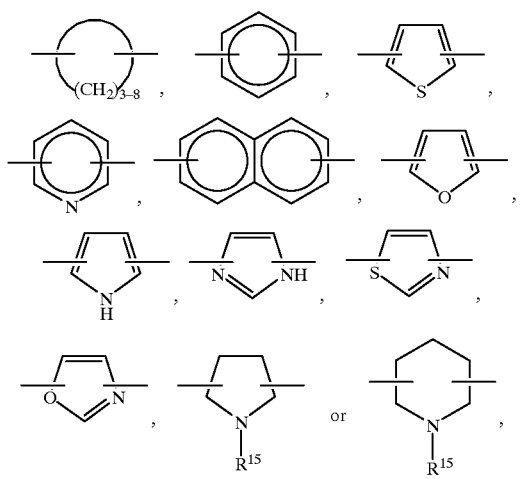

where $R^{15}$ is H, $C_1$-$C_8$ alkyl, $C_1$-$C_{20}$ alkylcarbonyl, $C_1$-$C_{20}$ alkoxycarbonyl, or benzyl; or A together with $R^3$ and the interposed nitrogen form a heterocyclic moiety of the formula:

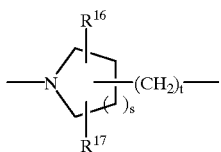

where s is 0, 1, 2, 3 or 4, t is 0 to 15, and $R^{16}$ and $R^{17}$ are, independently, hydrogen, $C_1-C_8$ alkyl, $C_1-C_8$ alkoxy, $C_1-C_8$ alkylcarbonyl, hydroxy, cyano, $C_1-C_8$ alkylcarbonyloxy, or $-(CH_2)_{0-6}-NR^{18}R^{19}$ where $R^{18}$ is $C_1-C_8$ alkyl, $C_1-C_8$ alkoxycarbonyl, or $C_1-C_8$ alkylcarbonyl and $R^{19}$ is hydrogen or $C_1-C_8$ alkyl;

$R^1$ and $R^2$ are independently hydrogen, $C_1-C_8$ alkyl, $C_1-C_8$ alkoxy, $C_1-C_8$ alkylcarbonyl, hydroxy, cyano, $C_1-C_8$ alkylcarbonyloxy, or $-(CH_2)_{0-6}-NR^{18}R^{19}$ where $R^{18}$ is $C_1-C_8$ alkyl, $C_1-C_8$ alkoxycarbonyl, or $C_1-C_8$ alkylcarbonyl and $R^{19}$ is hydrogen or $C_1-C_8$ alkyl;

$R^3$ is H, $C_1-C_8$ alkyl or $C_7-C_{15}$ arylalkyl where aryl is phenyl optionally substituted with a $C_1-C_6$ alkyl group or is combined with A to form a heterocyclic ring as described above;

$R^4$ and $R^5$ are independently hydrogen, $C_1-C_{20}$ alkyl, $C_2-C_{20}$ alkenyl, $C_3-C_{10}$ cycloalkyl,

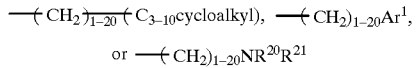

where $R^{20}$ is $C_1-C_{20}$ alkyl, $C_2-C_{20}$ alkenyl, $C_1-C_{20}$ alkylcarbonyl, $C_1-C20$ alkoxycarbonyl or benzyl; and $R^{21}$ is hydrogen or $C_1-C_{20}$ alkyl, wherein $Ar^1$ is defined above, or $R^4$ and $R^5$ together with the interposed nitrogen form a heterocyclic moiety of the formula:

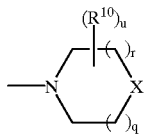

where r, q, u, $R^{10}$ and X are as defined above, or a pharmaceutically acceptable salt thereof.

In the preceding group of compounds, the preferred values for Z are:

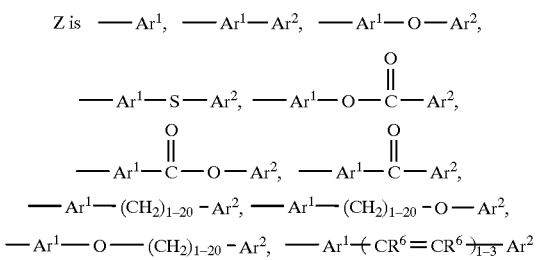

where $R^6$ is H or $C_1-C_8$ alkyl, or $-Ar^1NR^7-Ar^2$ where $R^7$ is hydrogen, $C_1-C_8$ alkyl, $C_1-C_8$ alkylcarbonyl or $C_1-C_8$ alkoxycarbonyl and $Ar^1$ and $Ar^2$ are selected from phenyl, naphthyl, furanyl, benzofuranyl, dibenzofuranyl, pyridinyl, thienyl, benzothienyl, imidazolyl, oxazolyl, benzoxazolyl, thiazolyl, benzthiazolyl, isoxazolyl, benzisoxazolyl, indenyl, indolyl, quinolinyl, isoquinolinyl, carbazolyl, benzimidazolyl or fluorenyl; and $Ar^1$ and $Ar^2$ may be optionally substituted by fluorine, chlorine, bromine, iodine, cyano, nitro, $-CO_2H$, $C_1-C_8$ alkyl, $C_1-C_8$ alkoxy, $C_2-C_8$ alkenyl, trifluoromethyl, $C_3-C_8$ cycloalkyl, $C_3-C_8$ cycloalkyloxy, $C_1-C_8$ alkylcarbonyl, $C_1-C_8$ alkoxycarbonyl, $C_1-C_8$ alkylcarbonyloxy, $-NH_2$, $-(CH_2)_{1-6}-NR^8R^9$ where $R^8$ is $C_1-C_8$ alkyl, $C_1-C_8$ alkylcarbonyl or $C_1-C_8$ alkoxycarbonyl, and $R^9$ is hydrogen or $C_1-C_8$ alkyl.

The preferred values for A in the generic description of the compounds of this invention is:

A is a bridging group selected from:

a saturated or unsaturated, straight or branched hydrocarbon chain of 1 to 20 carbon atoms which may have 1 to 6 sites of olefinic and/or acetylenic unsaturation;

a group of the formula:

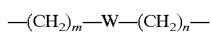

where m and n are 1 to 19, m+n is 2 to 20 and W is a group selected from $-O-$, $-S-$, or $-NR^{14}-$ where $R^{14}$ is hydrogen, $C_1-C_8$ alkyl, $C_1-C_8$ alkylcarbonyl, $C_1-C_8$ alkoxycarbonyl or benzyl;

a group of the formula:

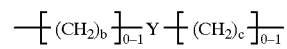

where b and c are 1 to 20, b+c is 1 to 20, and Y is selected from the group consisting of:

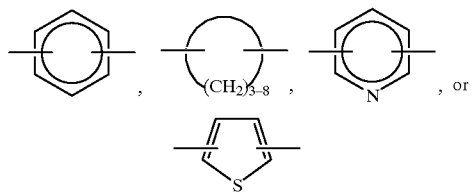

or A together with $R^3$ and the interposed nitrogen form a heterocyclic moiety of the formula:

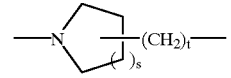

where s is 0, 1, 2 or 3 and t is 0 to 15.

In addition, the preferred values for $R^4$ and $R^5$ are, independently, hydrogen, $C_1-C_{12}$ alkyl, $C_2-C_8$ alkenyl, $C_3-C_8$ cycloalkyl, $-(CH_2)_{1-10}-(C_3-C_{10}$ cycloalkyl), $-(CH_2)_{1-10}Ar^1$, $-(CH_2)_{1-10}-NR^{20}R^{21}$ where $R^{20}$ is $C_1-C_8$ alkyl, $C_2-C_8$ alkenyl, $C_1-C_8$ alkylcarbonyl, $C_1-C_8$ alkoxycarbonyl or benzyl, and $R^{21}$ is hydrogen or $C_1-C_8$ alkyl, or $R^4$ and $R^5$ together with the interposed nitrogen forms a heterocyclic moiety of the formula:

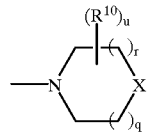

where q is 0, 1 or 2, r is 1 or 2, u is 0, 1 or 2, $R^{10}$ is $C_1-C_8$ alkyl and X is $-O-$, $-S-$, $-NR^{11}-$ where $R^{11}$ is hydrogen, $C_1$–$C_8$ alkyl or benzyl or X is $CR^{12}R^{13}$ where $R^{12}$ is hydrogen, hydroxy, $C_1$–$C_8$ alkyl, $C_1$–$C_8$ alkoxy, and $R^{13}$ is hydrogen or $C_1$–$C_8$ alkyl, or $R^{12}$ and $R^{13}$ together with the interposed carbon forms a 3 to 8 membered carbocyclic ring.

In the above description of the novel compounds of this invention, the term alkyl encompasses branched as well as straight chain hydrocarbons; and the term alkenyl includes branched and straight chain alkenes having from 1 to 3 double bonds. The term "alkoxy" refers to the alkyl-O— moiety. The number and position of substituents on an $Ar^1$ or $Ar^2$ group is governed by the size of the substituent and availability, either commercially or prepared by standard literature procedures and such limitations would be recognized by one skilled in the art of organic synthesis. In general, 1 to 3 substituents would be allowable with the exception of fluorine or chlorine where up to 5 fluorines or chlorines may be present as when the starting material for Z is pentafluorophenol. The term pharmaceutically acceptable salts encompasses acid addition salts that may be formed from a basic invention compound and a pharmaceutically acceptable inorganic or organic acid such as hydrochloric, sulfuric, phosphoric, acetic, maleic, fumaric, succinic, citric, tartaric, methanesulfonic acids and the like; a basic salt formed from an acidic invention compound and a pharmaceutically acceptable metal cation such as sodium, potassium, magnesium or calcium, the ammonium salt or an amine salt such as the triethylamine salt, or a quarternary salt formed from a basic invention compound and a pharmaceutically acceptable alkyl or aralkyl halide such as methylbromide or benzylbromide. The compounds of this invention may be recovered in the form of a solvate or hydrate. It is understood that the name of the compound itself emcompases these simple solvates.

DETAILED DESCRIPTION OF THE INVENTION

The compounds of this invention are most conveniently prepared by reacting an intermediate hydroxy compound with phosgene or a phosgene equivalent followed by adding an appropriate amine or amine hydrochloride in the presence of a base in a suitable solvent. The preferred phosgene equivalent is 4-nitrophenyl chloroformate and the most suitable solvents are methylene chloride, chloroform and dimethylformamide. When convenient, an isocyanate or carbamoyl chloride can be prepared and reacted directly with the alcohol to give the desired carbamates ($R^4 \neq H$) outlined in Scheme II. The preferred synthetic route is illustrated in Scheme I.

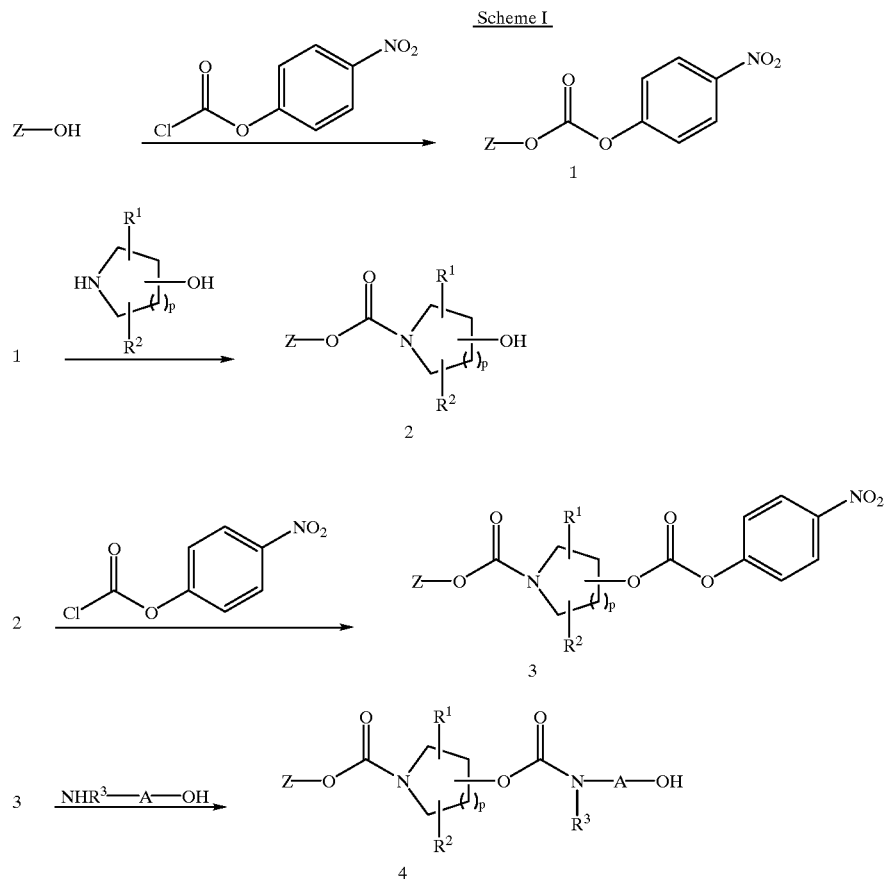

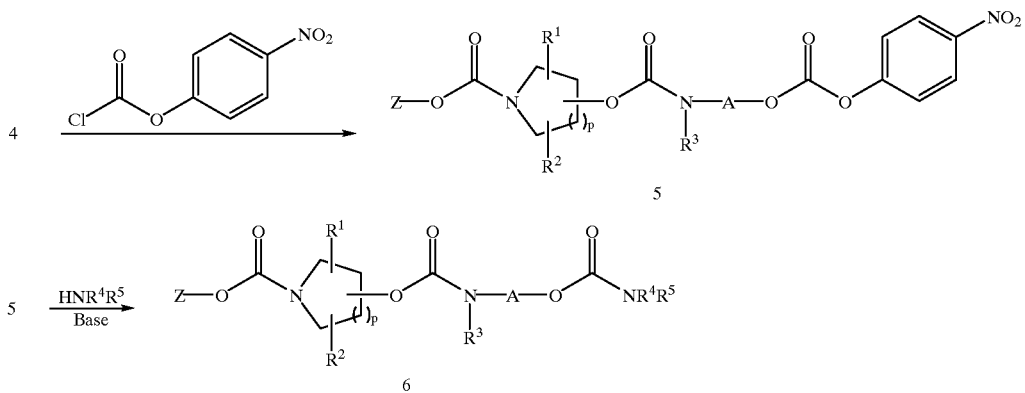

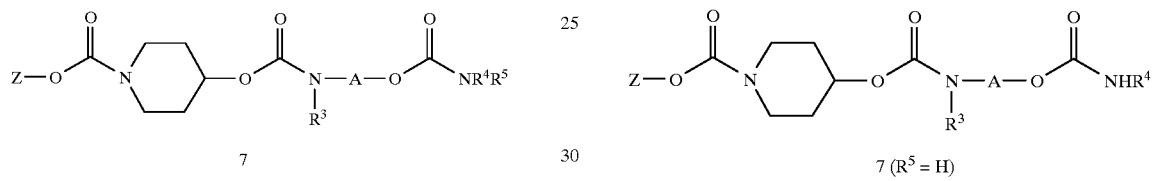

Preferred compounds of this invention are of formula 6 where p is 2, $R^1$ and $R^2$ are H, and the preferred compounds therefore have the following formula:

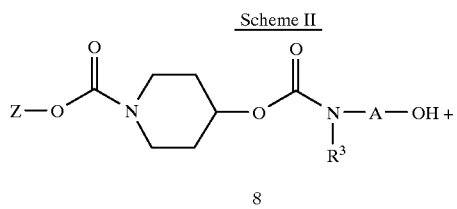

The preferred piperidine dicarbamate structure 8 is used to illustrate the use of an isocyanate to make the compounds of this invention.

Scheme II

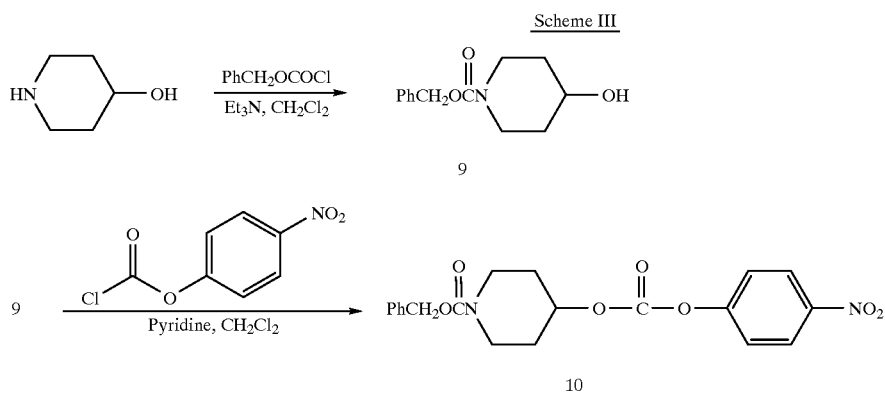

Scheme III outlines a convenient synthetic method for preparing invention compounds 7 from a prepared common intermediate 14 where the moiety Z is to be varied. For illustrative purposes in Scheme III, A is —$(CH_2)_6$— and $NR^4R^5$ is 8-azaspiro[4,5]decane-8yl. Z may be activated by a variety of methods known in the art of organic sythesis. One such method is illustrated in Scheme III. Another method of activating Z is as its chloroformate as illustrated in Example 26.

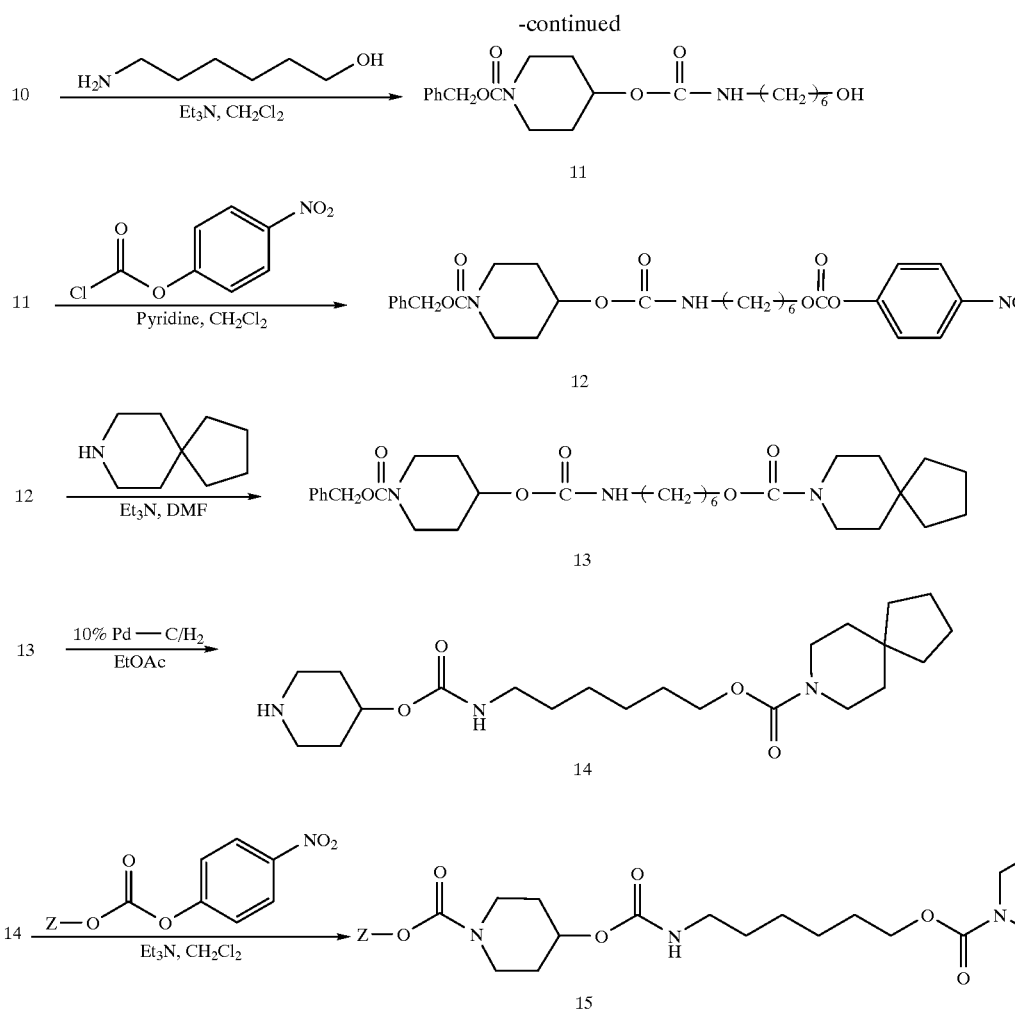

In the above outlined synthetic procedures of Schemes I–III where a hydroxyl, amino, or carboxyl substituent is present and not utilized in the carbamate forming reactions, the hydroxyl, amino, or carboxyl group may be protected by a removable protecting group. The protected form is recommended where the hydroxyl, amino, or carboxyl group may otherwise undergo an undesired reaction. Protecting groups for hydroxyl, amino, or carboxyl groups are given in J. F. W. McOmie, Protective Groups in Organic Chemistry (Plenum Press, 1973) and T. W. Greene, Protective Groups in Organic Chemistry (John Wiley and Sons, 1981). The protecting group may be removed at a suitable later stage in the synthetic scheme during the course of synthesis of end products.

The following specific examples for the synthesis of intermediates and invention compounds are included for illustrative purposes only and are not to be construed as limiting to this disclosure in any way. Those skilled in the art will be aware of other methods of preparing compounds of this invention. The starting materials or intermediates are available commercially or can be prepared following standard literature procedures.

EXAMPLE 1

Carbonic Acid (4-nitrophenyl) ester (4-phenoxyphenyl) ester

A solution of 4-phenoxyphenol (50 g, 0.27 mol) and pyridine (22 mL, 0.27 mol) in 500 mL of methylene chloride was added under nitrogen dropwise over 1.5 hours to a solution of 4-nitrophenyl chloroformate (54 g, 0.27 mol) in 500 mL of methylene chloride at room temperature. After the addition the reaction was stirred overnight at room temperature. The reaction was extracted two times with 1N HCl, multiple times with saturated $Na_2CO_3$, dried ($MgSO_4$) and the solvent removed under reduced pressure to give 94.86 g of a light yellow crystalline solid. Recrystallization from methylene chloride-diisopropyl ether gave 69.13 g (73%) of the title compound as a light tan crystalline solid, mp 113–115° C.

Analysis Calc'd for $C_{19}H_{13}NO_6$: C, 64.96; H, 3.73; N, 3.99 Found: C, 64.63; H, 3.89; N, 3.93

EXAMPLE 2

4-Hydroxy-1-piperidinecarboxylic acid 4-phenoxyphenyl ester

A solution of the carbonate(45 g, 0.13 mol) produced in Example 1 in 250 mL of methylene chloride was added dropwise under nitrogen over three hours to a solution of 4-hydroxypiperidine (14.3 g, 0.14 mol) and triethylamine (19.7 mL, 0.14 mol) in 250 mL of methylene chloride at ice bath temperature. After the addition the reaction was stirred at ice bath temperature for 4 hours and at room temperature overnight. The reaction was extracted one time with 1N HCl and then multiple times with saturated $Na_2CO_3$, dried (MgSO$_4$) and the solvent removed under reduced pressure to give 39.27 g of a light yellow solid. Recrystallization from diisopropyl ether-methanol gave 31.78 g (79%) of the title compound as an off-white crystalline solid, mp 130–133° C.

Analysis Calc'd for C$_{18}$H$_{19}$NO$_4$: C, 69.00; H, 6.11; N, 4.47 Found: C, 68.90; H, 6.18; N, 4.45

EXAMPLE 3

4-(4-Nitro-phenoxycarbonyloxy)-piperidine-1-carboxylic acid 4-phenoxyphenyl ester A solution of the alcohol (25 g, 80 mmol) produced in Example 2 and pyridine (6.4 mL, 80 mmol) in 300 mL of methylene chloride was added under nitrogen dropwise over one hour to a solution of 4-nitrophenyl chloroformate (16.1 g, 80 mmol) in 200 mL of methylene chloride at ice bath temperature. The reaction was stirred at ice bath temperature for two hours and then overnight at room temperature. The reaction was extracted one time with 1N HCl, two times with saturated Na$_2$CO$_3$, dried (MgSO4) and the solvent removed under reduced pressure to give 37.3 g of an off-white solid. Recrystallization from 1:1 ethyl acetate: hexane gave 26.4 g (69%) of the title compound as an off-white solid, mp 108–109° C.

Analysis Calc'd for C$_{25}$H$_{22}$N$_2$O$_8$: C, 62.76; H, 4.63; N, 5.86 Found: C, 62.99; H, 4.53; N, 5.85

EXAMPLE 4

4-[[[(6-Hydroxyhexyl)amino]-carbonyl]oxy]-1-piperidinecarboxylic acid 4-phenoxyphenyl ester A solution of triethylamine (65.5 mL, 0.47 mol) and 6-aminohexanol (13.2 g, 0.11 mol) in 300 mL of methylene chloride was added dropwise under nitrogen to a solution of the carbonate (45.0 g, 0.09 mol) produced in Example 3 in 500 mL of methylene chloride at room temperature. After the addition the solution was stirred at room temperature overnight. The reaction was extracted one time with 1N HCl and then multiple times with saturated Na$_2$CO$_3$, dried (MgSO$_4$) and the solvent removed under reduced pressure to give 47.0 g of an off-white solid. Recrystallization from methylene chloride-diisopropyl ether gave 35.5 g (83%) of the title compound as a white crystalline solid, mp 69–72° C.

Analysis Calc'd for C$_{25}$H$_{32}$N$_2$O$_6$: C, 65.77; H, 7.07; N, 6.14 Found: C, 65.49; H, 7.05; N, 5.85

EXAMPLE 5

4-[6-(4-Nitro-phenoxycarbonyloxy)-hexylcarbamoyloxy]-piperidine-1-carboxylic acid 4-phenoxyphenyl ester A solution of the alcohol (40.0 g, 88 mmol) produced in Example 4 and pyridine (7.1 ml, 88 mmol) in 300 ml of methylene chloride was added under nitrogen dropwise over one hour to a solution of 4-nitrophenyl chloroformate (17.7 g, 88 mmol) in 300 ml of methylene chloride at ice bath temperature. The reaction was stirred at ice bath temperature for two hours and overnight at room temperature. The reaction was extracted one time with 1N HCl, multiple times with saturated Na$_2$CO$_3$, dried (MgSO$_4$) and the solvent removed under reduced pressure to give 54.9 g of an off-white solid. Recrystallization from 1:1 ethyl acetatehexane gave 51.6 g (95%) of the title compound as a white crystalline solid, mp 117–120° C.

Analysis Calc'd for C$_{32}$H$_{35}$N$_3$O$_{10}$: C, 61.83; H, 5.68; N, 6.76 Found: C, 61.01; H, 5.65; N, 6.66

EXAMPLE 6

4-[6-(Hexylcarbamoyloxy)-hexylcarbamoyloxy]-piperidine-1-carboxylic acid 4-phenoxyphenyl ester A solution of the carbonate (35.0 g, 56 mmol) produced in Example 5 in 400 mL of methylene chloride was added dropwise under nitrogen to a solution of hexylamine (8.9 mL, 67 mmol) and triethylamine (39.2 mL, 281 mmol) in 400 mL of methylene chloride at ice bath temperature. After the addition the reaction was stirred at room temperature until it was judged complete by thin layer chromatographic analysis (TLC). If necessary, additional quantities of hexylamine and triethylamine can be added to drive the reaction to completion. The reaction was extracted one time with 1N HCl, multiple times with saturated Na$_2$CO$_3$, dried (MgSO$_4$) and the solvent removed under reduced pressure to give 30.9 g of a white solid. Recrystallization from methylene chloride-diisopropyl ether gave 27.6 g (84%) of the title compound as a white crystalline solid, mp 79–800° C.

Analysis Calc'd for C$_{32}$H$_{45}$N$_3$O$_7$: C, 65.84; H, 7.77; N, 7.20 Found: C, 65.83; H, 7.80; N, 7.13

EXAMPLE 7

4-[6-(Dihexyl-carbamoyloxy)-hexylcarbamoyloxy-piperidine-1-carboxylic acid 4-phenoxyphenyl ester A solution of the carbonate (2.0 g, 3.2 mmol) produced in Example 5 in 30 ml of methylene chloride was added dropwise under nitrogen to a solution of dihexylamine (900 μl, 3.9 mmol) and triethylamine (2.7 ml, 16 mmol) in 30 ml of methylene chloride at ice bath temperature. The reaction was stirred at ice bath temperature for approximately one hour and then overnight at room temperature. The reaction was extracted one time with 1N HCl, multiple times with saturated Na$_2$CO$_3$, dried (MgSO$_4$) and the solvent removed under reduced pressure to give 2.35 g of a yellow oil. Purification of the oil by chromatography on 230 g of silica gel (230–400 mesh) using 10% ethyl acetate-methylene chloride as the eluent gave 1.90 g (88%) of the title compound as a clear oil, MS m/e 668 (M+H)$^+$.

Analysis Calc'd for C$_{38}$H$_{57}$N$_3$O$_7$: C, 68.34; H, 8.60; N, 6.29 Found: C, 68.63; H, 8.69; N, 6.30

EXAMPLE 8

4-[6-(Piperidine-1-carbonyloxy)-hexylcarbamoyloxy]-piperidine-1-carboxylic acid 4-phenoxyphenyl ester A solution of the carbonate (2.0 g, 3.2 mmol) produced in Example 5, piperidine (0.38 mL, 3.9 mmol) and triethylamine (2.2 mL, 16 mmol) in 30 mL of anhydrous dimethylformamide was stirred under nitrogen at room temperature overnight. The reaction was diluted with methylene chloride, extracted one time with 1N HCl, multiple times with saturated Na$_2$CO$_3$, dried (MgSO$_4$) and the solvent removed under reduced pressure to give 1.76 g of a white solid. Recrystallization from methylene chloride-diisopropyl ether gave 0.85 g (46%) of the title compound as a white crystalline solid, mp 92–93° C.

Analysis Calc'd for C$_{31}$H$_{41}$N$_3$O$_7$: C, 65.59; H, 7.28; N, 7.40 Found: C, 65.49; H, 7.32; N, 7.11

EXAMPLE 9

4-[6-Dibenzyl-carbamoyloxy)-hexyl-carbamoyloxy]-piperidine-1-carboxylic acid 4-phenoxyphenyl ester A solution of the carbonate (2.0 g, 3.2 mmol) produced in Example 5 in 50 mL of chloroform (free of ethanol) was added dropwise under nitrogen to a solution of dibenzylamine (0.74 mL, 3.9 mmol) and triethylamine (2.2 mL, 16 mmol) in 50 mL of chloroform at ice bath temperature. After the addition the solution was heated to reflux and the reaction monitored by TLC. The reaction was extracted one time with 1N HCl, multiple times with saturated $Na_2CO_3$, dried ($MgSO_4$) and the solvent removed under reduced pressure to give 2.30 g of a brown oil. Purification on 250 g of silica gel (230–400 mesh) using ethyl acetate-methylene chloride as an eluent gave 1.56 g of an oil. Crystallization of the oil from diisopropyl ether gave 1.16 g (53%) of the diisopropyl etherate of the title compound as a white crystalline solid, mp 68–70° C.

Analysis Calc'd $C_{40}H_{45}N_3O_7 \cdot 0.1$ mole diisopropyl ether: C, 70.68; H, 6.78; N, 6.09 Found: C, 70.85; H, 6.71; N, 5.87

EXAMPLE 10

4-[12-(Hexylcarbamoyloxy)-dodecylcarbamoyloxy]-piperidine-1-carboxylic acid 4-phenxoyphenyl ester A mixture of the carbonate (11.0 g, 23 mmol) produced in Example 3, 12-aminododecanoic acid (5.9 g, 28 mmol) and triethylamine (16.0 mL, 110 mmol) in 300 mL of anhydrous dimethylformamide was stirred under nitrogen at approximately 70° C. for 3 hours. The reaction was diluted with ethyl acetate, extracted two times with 1N HCl, multiple times with water, dried ($MgSO_4$) and the solvent removed under reduced pressure to give 16.3 g of an off-white solid. Purification on 400 g of silica gel (230–400 mesh) using 10% EtOAc-$CH_2Cl_2$ to remove the nitrophenol and then 5% MeOH-$CH_2Cl_2$ to remove the desired product gave, after removal of the solvent under reduced pressure, 4-(11-carboxy-undecylcarbamoyloxy)-piperidine-1-carboxylic acid 4-phenoxyphenyl ester (11.2 g, 88%) as a white crystalline solid, mp 88–90° C.

Analysis Calc'd for $C_{31}H_{42}N_2O_7$: C, 67.12; H, 7.63; N, 5.05 Found: C, 67.28; H, 7.60; N, 4.80

A 1M solution of $BH_3 \cdot THF$ in THF (14.4 mL, 14.4 mmol) was added under nitrogen dropwise over 30 minutes to a solution of the acid (8.0 g, 14.4 mmol) produced in the previous step in 250 mL of anhydrous THF at ice bath temperature. The reaction was stirred at ice bath temperature for 1 hour and overnight at room temperature. By TLC analysis the reaction was not complete. An additional 21.6 mL (21.6 mmol) of the $BH_3 \cdot THF$ was added and the solution stirred at room temperature until the reaction was complete by TLC. The reaction was quenched by the addition of 60 mL of 1N HCl. After stirring at room temperature for 15 minutes the THF was removed under reduced pressure and the residue partitioned between 1N HCl and EtOAc. The organic layer was separated, washed one additional time with 1N HCl, dried ($MgSO_4$) and the solvent removed under reduced pressure to give 7.43 g of a white solid. Purification on 800 g of silica gel (230–400 mesh) using hexane-ethyl acetate as an eluent and recrystallization from diisopropyl ether-methylene chloride gave 4-(12-hydroxy-dodecylcarbamoyloxy)-piperidine-1-carboxylic acid 4-phenoxyphenyl ester (3.88 g, 50%) as a white crystalline solid, mp 75–76° C.

Analysis Calc'd for $C_{31}H_{44}N_2O_6$: C, 68.86; H, 8.20; N, 5.18 Found: C, 68.65; H, 8.24; N, 5.09

A solution of the alcohol (1.00 g, 1.86 mmol) produced in the previous step and pyridine (150 μl, 1.85 mmol) in 30 ml of methylene chloride was added under nitrogen dropwise over one hour to a solution of 4-nitrophenyl chloroformate (0.37 g, 1.85 mmol) in 10 ml of methylene chloride at ice bath temperature. The reaction was stirred at ice bath temperature for 3.5 hours and then overnight at room temperature. The reaction was extracted one time with 1N HCl, multiple times with saturated $Na_2CO_3$, dried ($MgSO_4$) and the solvent removed under reduced pressure to give 1.26 g of a white crystalline solid. Purification of the solid on 300 g of silica gel (230–400 mesh) using 25% ethyl acetate-hexane as the eluent gave 979 mg (75%) of 4-[12-(4-nitrophenoxycarbonyloxy)-dodecylcarbamoyloxy]-piperidine-1-carboxylic acid 4-phenoxyphenyl ester as a white crystalline solid, mp 96–98° C.

Analysis Calc'd for $C_{38}H_{47}N_3O_7$: C, 64.67; H, 6.71; N, 5.95 Found: C, 64.74; H, 6.67; N, 5.77

A solution of triethylamine (882 μl, 6.33 mmol) and 6-hexylamine (200 μl, 1.51 mmol) in 20 ml of methylene chloride was added dropwise under nitrogen to a solution of the carbonate (893 mg, 1.27 mmol), produced in the previous step, in 20 ml of methylene chloride at ice bath temperature. After the addition, the reaction was stirred at ice bath temperature for two hours and at room temperature for approximately three days. The reaction was extracted one time with 1N HCl, multiple times with saturated $Na_2CO_3$, dried ($MgSO_4$) and the solvent removed under reduced pressure to give 799 mg of a white crystalline solid. Purification of this solid by recrystallization from methylene chloride-diisopropyl ether gave 734 mg (87%) of the title compound as a white crystalline solid, mp 98–100° C.

Analysis Calc'd for $C_{38}H_{57}N_3O_7$: C, 68.34; H, 8.60; N, 6.29 Found: C, 68.33; H, 8.59; N, 6.21

EXAMPLE 11

4-{6-[(4-(2,2-Dimethyl-propyl)-benzyl)-heptyl-carbamoyloxy]-hexyl-carbamoyloxy}-piperidine-1-carboxylic acid 4-phenoxyphenyl ester A solution of the carbonate (2.0 g, 3.2 mmol) produced in Example 5, 4-(2,2-dimethyl-propyl)-benzyl-heptylamine (1.1 g, 3.9 mmol) and triethylamine (2.2 ml, 16 mmol) in 30 ml of anhydrous dimethylformamide was stirred under nitrogen at room temperature overnight. The reaction was diluted with methylene chloride, extracted one time with 1N HCl, multiple times with saturated $Na_2CO_3$, dried ($MgSO_4$) and the solvent removed under reduced pressure to give 2.73 g of a light brown oil. Purification of this oil by chromatography on silica gel (230–400 mesh) using 10% ethyl acetate-methylene chloride as the eluent gave 2.11 g (87%) of the title compound as a clear oil, MS m/e 758 $(M+H)^+$.

Analysis Calc'd for $C_{45}H_{63}N_3O_7$: C, 71.30; H, 8.38; N, 5.54 Found: C, 71.01; H, 8.34; N, 5.14

EXAMPLE 12

8-Aza-spiro[4,5]decane-8-carboxylic acid 6-{[1-(4-phenoxy-phenoxycarbonyl)-piperidine-4-oxycarbonyl]amino}-hexyl ester A solution of the carbonate (2.0 g, 3.2 mmol) produced in Example 5, 8-aza-spiro[4,5]-decane hydrochloride (680 mg, 3.9 mmol) and triethylamine (2.7 ml, 19 mmol) in 30 ml of anhydrous dimethylformamide was stirred under nitrogen at room temperature for 5 hours. The reaction was diluted with methylene chloride, extracted one time with 1N HCl, multiple times with saturated $Na_2CO_3$, dried ($MgSO_4$), and the solvent removed under reduced pressure to give 1.85 g of a white solid. Recrystallization of this solid from methylene chloride-diisopropyl ether gave 1.0 g (50%) of the title compound as a white crystalline solid, mp 83–85° C.

Analysis Calc'd for $C_{35}H_{47}N_3O_7$: C, 67.61; H, 7.62; N, 6.76 Found: C, 67.83; H, 7.70; N, 6.48

EXAMPLE 13

(Z)-4-6-(octadec-9-enylcarbamoyloxy)-hexylcarbamoyloxy]-piperidine-1-carboxylic acid 4-phenoxyphenyl ester A solution of the carbonate (2.0 g, 3.2 mmol), produced in Example 5, in 30 ml of methylene chloride was added dropwise under nitrogen to a solution of oleylamine (1.6 ml, 3.9 mmol) and triethylamine (2.2 ml, 16 mmol) in 30 ml of methylene chloride at ice bath temperature. After the addition, the reaction was stirred at ice bath temperature for approximately one hour and then overnight at room temperature. The reaction was extracted one time with 1N HCl, multiple time with saturated $Na_2CO_3$, dried ($MgSO_4$) and the solvent removed under reduced pressure to give 2.65 g of a light yellow solid. Purification of this solid on 300 g of silica gel (230–400 mesh) using 10% $EtOAc$-$CH_2Cl_2$ as the eluent gave 2.02 g (84%) of the title compound as a white crystalline solid, mp 74–76° C.

Analysis Calc'd for $C_{44}H_{67}N_3O_7$: C, 70.46; H, 9.00; N, 5.60 Found: C, 70.01; H, 8.91; N, 5.75

EXAMPLE 14

(Z)-4-[12-(Octadec-9-enylcarbamoyloxy)-dodecylcarbamoyloxy]-piperidine-1-carboxylic acid 4-phenoxyphenyl ester A solution of the carbonate (1.5 g, 2.1 mmol) produced in Example 10, in 30 ml of methylene chloride was added dropwise under nitrogen to a solution of oleylamine (1.0 ml, 2.6 mmol) and triethylamine (1.5 ml, 11 mmol) in 30 ml of methylene chloride at ice bath temperature. After the addition, the reaction was stirred at ice bath temperature for approximately one hour and then overnight at room temperature. The reaction was extracted one time with 1N HCl, multiple times with saturated $Na_2CO_3$, dried ($MgSO_4$) and the solvent removed under reduced pressure to give 2.19 g of a yellow solid. Recrystallization of the solid from diisopropyl ether gave 1.47 g (83%) of the title compound as a crystalline solid, mp 83–84° C.

Analysis Calc'd for $C_{50}H_{79}N_3O_7$: C, 71.99; H, 9.55; N, 5.04 Found: C, 72.25; H, 9.70; N, 4.98

EXAMPLE 15

4-[[[(3-Hydroxypropyl)amino]carbonyl]oxy]-1-piperidinecarboxylic acid 4-phenoxyphenyl ester A solution of the carbonate (10.0 g, 21 mmol) produced in Example 3 in 50 mL of methylene chloride was added dropwise over 1 hr under nitrogen to a solution of triethylamine (14.6 mL, 100 mmol) and 3-aminopropanol (1.9 mL, 25 mmol) in 25 mL of methylene chloride at ice bath temperature. After the addition the solution was stirred at ice bath temperature for 1 hr and then at room temperature overnight. The reaction was extracted one time with 1N HCl and then multiple times with saturated $Na_2CO_3$, dried ($MgSO_4$) and the solvent removed under reduced pressure to give 8.23 g of a white solid. Trituration with hot diisopropyl ether gave 7.56 g (87%) of the title compound as a white crystalline solid, mp 81–83° C.

Analysis Calc'd for $C_{22}H_{36}N_2O_6$: C, 63.76; H, 6.32; N, 6.76 Found: C, 63.80; H, 6.40; N, 6.98

EXAMPLE 16

4-[3-(Hexylcarbamoyloxy)-propylcarbamoyloxy]-piperidine-1-carboxylic acid 4-phenoxyphenyl ester A solution of the alcohol (2.0 g, 4.8 mmol) produced in Example 15, triethylamine (540 µl, 3.9 mmol) and hexyl isocyanate (740 mg, 5.8 mmol) in 20 mL of $CHCl_3$ (EtOH free) was stirred under nitrogen at room temperature overnight. By TLC the reaction was not complete. An additional 610 mg (4.8 mmol) of hexyl isocyanate was added and the solution refluxed. The reaction was monitored by TLC. At the end of the reaction the solution was extracted two times with 1N HCl, dried ($MgSO_4$) and the solvent removed under reduced pressure to give 2.70 g of a white solid. Recrystallization from diisopropyl ether gave 2.10 g (80%) of the title compound as a white crystalline solid, mp 90–92° C.

Analysis Calc'd for $C_{29}H_{39}N_3O_7$: C, 64.31; H, 7.26; N, 7.76 Found: C, 64.38; H, 7.28; N, 7.67

EXAMPLE 17

4-[3-(4-Nitro-phenoxycarbamoyloxy)-propylcarbamoyloxy]-piperidine-1-carboxylic acid 4-phenoxyphenyl ester A solution of the alcohol (4.96 g, 12 mmol) produced in Example 15, and pyridine (970 µl, 12 mmol) in 50 ml of methylene chloride was added under nitrogen dropwise over thirty minutes to a solution of 4-nitrophenyl chloroformate (2.4 g, 12 mmol) in 30 ml of methylene chloride at ice bath temperature. After the addition, the reaction was stirred at ice bath temperature for one hour and overnight at room temperature. The reaction was extracted one time with 1N HCl, multiple times with saturated $Na_2CO_3$, dried ($MgSO_4$) and the solvent removed under reduced pressure to give 6.80 g of a white solid. Concentration of the mother liquor gave additional solid which was recrystallized from methylene chloride-diisopropyl ether to give an additional 2.02 g (29%) of the title compound, mp 97–100° C.

Analysis Calc'd for $C_{29}H_{29}N_3O_{10}$: C, 60.10; H, 5.04; N, 7.25 Found: C, 59.92; H, 4.92; N, 7.22

EXAMPLE 18

4-[3-(Nonylcarbamoyloxy)-propylcarbamoyloxy]-piperidine-1-carboxylic acid 4-phenoxyphenyl ester A solution of the carbonate (2.0 g, 3.4 mmol) produced in Example 17 in 20 mL of anhydrous dimethylformamide was added dropwise under nitrogen to a solution of nonylamine (760 µl, 4.1 mmol) and triethylamine (2.4 mL, 17 mmol) in 20 mL of anhydrous dimethylformamide at ice bath temperature. After the addition the solution was stirred at ice bath temperature for 2 hrs and at room temperature overnight. The reaction was diluted with ethyl acetate, extracted five times with water, one time with 1N HCl, five times with saturated $Na_2CO_3$, dried ($MgSO_4$) and the solvent removed under reduced pressure to give 1.94 g of an off-white solid. Recrystallization from diisopropyl ether gave 1.55 g (77%) of the title compound as a white crystalline solid, mp 89–91° C.

Analysis Calc'd for $C_{32}H_{45}N_2O_7$: C, 65.84; H, 7.77; N, 7.20 Found: C, 65.72; H, 7.84; N, 7.22

EXAMPLE 19

8-Aza-spiro[4,5]decane-8-carboxylic acid 6-{[1-(4-phenoxy-phenoxycarbonyl)-piperidine-4-oxycarbonyl]-amino}-propyl ester A solution of the carbonate (2.0 g, 3.5 mmol) produced in Example 17 in 20 ml of anhydrous dimethylformamide was added dropwise under nitrogen to a solution of 8-aza-spiro [4.5]decane (750 mg, 4.9 mmol) and triethylamine (2.9 ml, 21 mmol) in 20 ml of anhydrous dimethylformamide at ice bath temperature. After the addition, the reaction was stirred at ice bath temperature for approximately 2 hours and at room temperature overnight. The reaction was diluted with ethyl acetate, extracted four times with water, one time with 1N HCl, five times with saturated $Na_2CO_3$, dried ($MgSO_4$) and the solvent removed under reduced pressure to give 1.93 g of a yellow oil. The oil was chromatographed on 200 g of silica gel (230–400 mesh) using 30%–40% EtOAc-hexane as the eluent. The material isolated was then recrystallized from EtOAc-hexane to give 667 mg (33%) of the title compound as white crystalline solid, mp 92–93° C.

Analysis Calc'd for $C_{32}H_{41}N_3O_7$: C, 66.30, H, 7.13; N, 7.25 Found: C, 66.35; H, 7.23; N, 7.33

EXAMPLE 20

4-Hydroxy-piperidine-1-carboxylic acid benzyl ester

A solution of benzyl chloroformate (35.3 ml, 0.25 moles) in 25 ml of methylene chloride was added dropwise under nitrogen over three hours to a solution of 4-hydroxypiperidine (25 g, 0.25 moles) and triethylamine (34.5 ml, 0.25 moles) in 500 ml of methylene chloride at ice bath temperature. After the addition the reaction was stirred at ice bath temperature for four hours and at room temperature overnight. The reaction was then extracted two times with 1N HCl, dried ($MgSO_4$) and the solvent removed under reduced pressure to give 53.1 g (90%) of the tide compound as a light yellow oil.

Analysis Calc'd for $C_{13}H_{17}NO_3$: C, 66.36; H, 7.28; N, 5.95 Found: C, 65.77; H, 7.18; N, 5.35

EXAMPLE 21

4-(4-Nitro-phenoxycarbonyloxy)-piperidine-1-carboxylic acid benzyl ester

A solution of the alcohol (72.3 g, 0.31 moles) produced in Example 20 and pyridine (37.3 ml, 0.46 moles) in 300 ml of methylene chloride was added dropwise under nitrogen over two hours to a solution of 4-nitrophenyl chloroformate (92.8 g, 0.46 moles) in 600 ml of methylene chloride at room temperature. After the addition the reaction was stirred for two days at room temperature. The reaction was then extracted two times with 1N HCl, multiple times with saturated $Na_2CO_3$, dried ($MgSO_4$) and the solvent removed under reduced pressure. Recrystallization of the crude product from methylene chloride-diisopropyl ether gave the tide compound as a crystalline solid, mp 118–120° C.

Analysis Calc'd for $C_{20}H_{20}N_2O_7$: C, 60.00; H, 5.03; N, 7.00 Found: C, 59.82; H, 4.93; N, 7.00

EXAMPLE 22

4-(6-Hydroxy-hexylcarbamoyloxy)-piperidine-1-carboxylic acid benzyl ester

A solution of the carbonate (128.826 g, 0.322 moles) produced in Example 21 in 450 ml of methylene chloride was added dropwise under nitrogen to a solution of 6-amino-1-hexanol (56.6 g, 0.483 moles) and triethylamine (224.2 ml, 1.61 moles) in 2 L of methylene chloride at room temperature. After the addition the reaction was stirred overnight at room temperature. By TLC the reaction was not complete. An additional 37.7 g (0.322 moles) of 6-amino-1-hexanol and 224.2 ml (1.61 moles) of triethylamine were added and the stirring continued overnight. By TLC the reaction was complete. The reaction was extracted two times with 1N HCl, multiple times with saturated $Na_2CO_3$, dried ($MgSO_4$) and the solvent removed under reduced pressure to give 95.0 g (78%) of a yellow oil which crystallized on standing, mp 50–52° C.

Analysis Calc'd for $C_{20}H_{30}N_2O_5$: C, 63.47; H, 7.99; N, 7.40 Found: C, 63.68; H, 8.07; N, 7.42

EXAMPLE 23

4-[6-(4-Nitro-phenoxycarbonyloxy)-hexylcarbamoyloxy]-piperidine-1-carboxylic acid benzyl ester A solution of the alcohol (50 g, 0.13 moles) produced in Example 22 and pyridine (10.7 ml, 0.13 moles) in 500 ml of methylene chloride was added dropwise under nitrogen to a solution of 4-nitrophenyl chloroformate (26.64 g, 0.13 mol) in 500 ml of methylene chloride at room temperature. After the addition, the reaction was stirred overnight at room temperature. A solid had formed which was removed by filtration. The filtrate was extracted two times with 1N HCl, multiple times with saturated $Na_2CO_3$, dried ($MgSO_4$) and the solvent removed under reduced pressure. Recrystallization of the crude reaction product from hexane gave 27.9 g (39%) of the title compound as a light yellow crystalline solid, mp 78–80° C.

Analysis Calc'd for $C_{29}H_{33}N_3O_9$: C, 59.66; H, 6.12; N, 7.73 Found: C, 59.32; H, 6.14; N, 7.74

EXAMPLE 24

8-Aza-spiro[4,5decane-8-carboxylic acid 6-[2-(1-benzyloxycarbonyl-piperidin-4-yl)-oxycarbonylamino]-hexyl ester A solution of the carbonate (29.2 g, 54 mmol) produced in Example 23 in 300 ml of anhydrous dimethylformamide was added dropwise under nitrogen to a solution of 8-aza-spiro[4,5]decane (11.53 g, 83 mmol) and triethylamine (37.49 ml, 269 mmol) in 300 ml of anhydrous dimethylformamide at room temperature. After the addition the reaction was heated at 80° C. for 5 hrs. The reaction was diluted with methylene chloride, extracted one time with 1N HCl, multiple times with saturated $Na_2CO_3$, dried ($MgSO_4$) and the solvent removed under reduced pressure to give 26.11 g of a yellow oil. Purification on silica gel (230–400 mesh) using ethyl acetate-methylene chloride as an eluent gave a light yellow solid. Trituration of the solid one time with hexane gave 14.75 g (50%) of the title compound as a white crystalline solid, mp 76–79° C.

Analysis Calc'd for $C_{30}H_{45}N_3O_6$: C, 66.27; H, 8.34; N, 7.73 Found: C, 66.16; H, 8.41; N, 7.69

EXAMPLE 25

8-Aza-spiro[4,5]decane-8-carboxylic acid 6-(2-piperidin-4-yl-oxycarbonylamino)-hexyl ester A mixture of the carbamate (10.00 g, 18.4 mmol) produced in Example 24 and 2.0 g of 10% Pd-C in 150 ml of ethyl acetate was hydrogenated at room temperature and 45–50 psi for 18 hrs. The catalyst was removed by filtration through celite and the filtrate concentrated under reduced pressure to give 7.57 g of a light yellow oil. The oil was used in subsequent reactions without further purification.

Analysis Calc'd for $C_{22}H_{39}N_3O_4$: C, 64.52; H, 9.60; N, 10.26 Found: C, 63.43; H, 9.96; N, 10.13

EXAMPLE 26

8-Aza-spiro[4,5]decane-8-carboxylic acid 6-{[1-(4-nitro-phenoxycarbonyl)-piperidine-4-oxycarbonyl]-amino}-hexyl ester A solution of 4-nitrophenyl chloroformate (1.48 g, 7.32 mmol) in 25 ml of methylene chloride was added dropwise under nitrogen to a solution of the amine (3.00 g, 7.32 mmol) produced in Example 25 and triethylamine (5.10 ml, 36.6 mmol) in 50 ml of methylene chloride at room temperature. The reaction was stirred 3 hours at room temperature and then extracted one time with 1N HCl, multiple times with saturated $Na_2CO_3$, dried ($MgSO_4$) and the solvent removed under reduced pressure to give 3.844 g of yellow crystals. Purification on silica gel (230–400 mesh) using 30% ethyl acetate-methylene chloride as an eluent gave 2.195 g (52%) of the title compound as a white crystalline solid, mp 113–114° C.

Analysis Calc'd for $C_{29}H_{42}N_4O_8$: C, 60.61; H, 7.37; N, 9.75 Found: C, 60.61; H, 7.47; N, 9.67

EXAMPLE 27

Carbonic Acid (4-nitrophenyl)ester (2-dibenzofuranyl) ester

A solution of 2-hydroxydibenzofuran (25 g, 0.136 mol) and pyridine (11 ml, 0.136 mol) in 300 ml of methylene chloride was added under nitrogen dropwise over five hours to a solution of 4-nitrophenyl chloroformate (27.4 g, 0.136 mol) in 300 ml of methylene chloride at ice bath temperature. After the addition the reaction was stirred at room temperature overnight. The solid formed was collected by filtration to give 33.08 g of a light tan solid. The filtrate was extracted one time with 1N HCl, one time with saturated $Na_2CO_3$ (emulsion formed), dried ($MgSO_4$) and the solvent removed under reduced pressure to give an additional 14.30 g of a light tan solid. This solid was triturated two times with methylene chloride to give 7.39 g of a light tan solid which was combined with the original 33.08 g of solid. Recrystallization of the combined material from ethyl acetate gave 20.23 g (43%) of the title compound as a light tan crystalline solid, mp 183–185° C.

Analysis Calc'd for $C_{19}H_{11}NO_6$: C, 65.33; H, 3.17; N, 4.01 Found: C, 65.11; H, 3.32; N, 3.94

EXAMPLE 28

8-Aza-spiro[4,5]decane-8-carboxylic acid 6-{[1-(dibenzofuran-2-yloxycarbonyl)piperidin-4-yl]-oxycarbonylamino}-hexyl ester A solution of the carbonate (1.706 g, 4.88 mmol) produced in Example 27 in 30 ml of chloroform (EtOH free) was added under nitrogen dropwise to a solution of the amine (2.00 g, 4.88 mmol) produced in Example 25 and triethylamine (3.40 ml, 24.4 mmol) in 30 ml of chloroform at room temperature. After the addition the reaction was stirred overnight at room temperature. The reaction was extracted one time with 1N HCl, multiple times with saturated $Na_2CO_3$, dried ($MgSO_4$) and the solvent removed under reduced pressure to give 3.03 g of off-white crystals. Purification on silica (230–400 mesh) using ethyl acetate-methylene chloride as an eluent gave a white solid. Recrystallization of this solid from hexane-ethyl acetate gave 1.3979 g (46%) of the title compound as a white crystalline solid, mp 100–102° C.

Analysis Calc'd for $C_{35}H_{45}N_3O_7$: C, 67.83; H, 7.32; N, 6.78 Found: C, 67.73; H, 7.29; N, 6.78

EXAMPLE 29

Carbonic acid (4-nitrophenyl)ester (4-phenylphenyl) ester

A solution of 4-phenylphenol (25.0 g, 0.15 mol) and pyridine (11.89 ml, 0.15 mol) in 250 ml of methylene chloride were added dropwise under nitrogen to a solution of 4-nitrophenyl chloroformate (29.65 g, 0.15 mol) in 200 ml of methylene chloride at ice bath temperature. The reaction was stirred at ice bath temperature for approximately two hours and then overnight at room temperature. The reaction was extracted one time with 1N HCl, multiple times with saturated $Na_2CO_3$, dried ($MgSO_4$) and the solvent removed under reduced pressure to give 46.05 g of light yellow crystals. Recrystallization from methylene chloride-diisopropyl ether gave the title compound as light yellow crystals, mp 138–140° C.

Analysis Calc'd for $C_{19}H_{13}NO_5$: C, 68.06; H, 3.91; N, 4.18 Found: C, 67.99; H, 3.70; N, 4.03

EXAMPLE 30

8-Aza-spiro[4,5]decane-8-carboxylic acid 6-{[1-(4-phenyl-phenoxycarbonyl)-piperidine-4-oxycarbonyl]-amino}-hexyl ester A solution of the carbonate (0.941 g, 2.8 mmol) produced in Example 29 in 10 ml of anhydrous DMF was added dropwise under nitrogen to a solution of the amine (1.153 g, 2.8 mmol) produced in Example 25 and triethylamine (1.95 ml, 14.0 mmol) in 20 ml of anhydrous DMF at approximately −40° C. The reaction was stirred at −40° for approximately 5 hours and then at room temperature overnight. The reaction was diluted with methylene chloride, extracted one time with 1N HCl, multiple times with saturated $Na_2CO_3$, dried ($MgSO_4$) and the solvent removed under reduced pressure to give 1.2066 g of a yellow crystalline solid. Recrystallization from ethyl acetate gave the title compound as a white crystalline solid, mp 110–111° C.

Analysis Calc'd for $C_{35}H_{47}N_3O_6$: C, 69.40; H, 7.82; N, 6.94 Found: C, 69.36; H, 7.95; N, 6.94

EXAMPLE 31

Carbonic acid (4-nitrophenyl)ester (4-pentylphenyl) ester

A solution of 4-pentylphenol (20.1 g, 0.13 mol) and pyridine (10 ml, 0.13 mol) in 300 ml of methylene chloride was added under nitrogen dropwise over 45 minutes to a solution of 4-nitrophenyl chloroformate (25.28 g, 0.13 mol) in 200 ml of methylene chloride at room temperature. After the addition, the reaction was stirred overnight at room temperature. The reaction was extracted one time with 1N HCl, four times with saturated $Na_2CO_3$, dried ($MgSO_4$) and the solvent removed under reduced pressure to give 36.97 g of a yellow crytstalline solid. Purification of the solid on 450 g of silica gel (230–400 mesh) using 50–60% $CH_2Cl_2$-hexane as the eluent gave 11.58 g (28%) of the title compound as a yellow crystalline solid, mp 67–69° C.

Analysis Calc'd for $C_{18}H_{19}NO_5$: C, 65.64; H, 5.82; N. 4.25 Found: C, 65.90; H, 5.85; N, 4.18

EXAMPLE 32

8-Aza-spiro[4,5]decane-8-carboxylic acid 6-{[1-(4-pentyl-phenoxycarbonyl)-piperidine-4-oxycarbonyl]-amino}-hexyl ester A solution of the carbonate (2.21 g, 6.72 mmol) produced in Example 31 in 50 ml of methylene chloride was added dropwise under nitrogen over 45 minutes to a solution of the amine (3.0 g, 6.72 mmol; HCl salt) produced in Example 25, and triethylamine (4.68 ml, 33.6 mmol) in 75 ml of methylene chloride at ice bath temperature. After the addition, the reaction was stirred at ice bath temperature for one hour and then for two days at room temperature. The reaction was extracted one time with 1N HCl, four times with saturated $Na_2CO_3$, dried ($MgSO_4$) and the solvent removed under reduced pressure to give 3.79 g of a light yellow crystalline solid. The solid was chromatographed on 400 g of silica gel (230–400 mesh) using 1:1 EtOAc-hexane as the eluent. The title compound (3.07 g, 76%) was isolated as a white crystalline solid, mp 100–102° C.

Analysis Calc'd for $C_{34}H_{53}N_3O_6$: C, 68.08; H, 8.91; N, 7.00 Found: C, 68.17; H, 9.08; N, 7.03

EXAMPLE 33

4-[4-(Hexylcarbamoyloxymethyl)-benzylcarbamoyloxy]-piperidine-1-carboxylic acid 4-phenoxyphenyl ester A mixture of the carbonate (15.0 g, 31 mmol) produced in Example 3, 4-(aminomethyl)benzoic acid (5.7 g, 38 mmol), and triethylamine (21.8 ml, 160 mmol) in 100 ml of anhydrous dimethylformamide was stirred under nitrogen at 70° C. for two hours. The reaction was diluted with ethyl acetate, extracted with 1N HCl, multiple times with water, dried ($MgSO_4$) and the solvent removed under reduced pressure to give 18.5 g of a light tan solid. Recrystallization of the solid from ethyl acetate gave 9.08 g (59%) of the desired acid compound as a white crystalline solid, mp 165–167° C.

Analysis Calc'd for $C_{27}H_{26}N_2O_7$: C, 66.11; H, 5.34; N, 5.71 Found: C, 65.94; H, 5.31; N, 5.76

Diisopropylcarbodiimide (1.3 ml, 9.0 mmol) in 10 ml of methylene chloride was added under nitrogen dropwise to a solution of the acid (4.4 g, 9.0 mmol) produced in the previous step, N-hydroxysuccinimide (1.0 g, 9.0 mmol) and dimethylaminopyridine (1.1 g, 9.0 mmol) in 50 ml of methylene chloride at ice bath temperature. After the addition the reaction was stirred at ice bath temperature for 1 hour and at room temperature for 2 hours. The solid formed was removed by filtration. The filtrate was extracted with 1N HCl, 5% $NaHCO_3$, dried ($MgSO_4$) and the solvent removed under reduced pressure to give 6.92 g of a white solid. Purification of the solid on 400 g of silica gel (230–400 mesh) using ethyl acetate-methylene chloride as the eluent gave the desired succinimide ester (2.88 g, 55%) as a white crystalline solid, mp 141–145° C.

Analysis Calc'd for $C_{31}H_{29}N_3O_9$: C, 63.37; H, 4.97; N, 7.15 Found: C, 63.36; H, 5.08; N, 6.79

Sodium borohydride (420 mg, 11 mmol) was added under nitrogen to a solution of the ester (2.6 g, 4.4 mmol) produced in the previous step in 50 ml of THF at room temperature. The reaction was then stirred overnight. The excess sodium borohydride was destroyed with 1N HCl. The THF was removed under reduced pressure and the residue partitioned between 1N HCl and methylene chloride. The organic layer was separated. The aqueous layer was extracted two times with methylene chloride. The combined extracts were dried ($MgSO_4$) and the solvent removed under reduced pressure to give 2.14 g of a white foam. Purification of the foam on 200 g of silica gel (230–400 mesh) using ethyl acetate-methylene chloride as the eluent gave the desired alcohol (991 mg, 47%) as a white crystalline solid, mp 97–101° C.

Analysis Calc'd for $C_{27}H_{28}N_2O_6$: C, 68.05; H, 5.92; N, 5.88 Found: C, 67.87; H, 5.84; N, 5.76

A solution of the alcohol (900 mg, 1.89 mmol) produced in the previous step, triethylamine (210 µl, 1.51 mmol) and hexyl isocyanate (528 mg, 4.15 mmol) in 20 ml of $CHCl_3$ (EtOH free) was refluxed under nitrogen overnight. By TLC starting material remained. An additional 240 mg (1.89 mmol) of hexyl isocyanate was added and the reaction was refluxed overnight. The reaction was extracted two times with 1N HCl, dried ($MgSO_4$) and the solvent removed under reduced pressure to give 1.58 g of a white solid. Recrystallization of the solid from EtOAc-diisopropyl ether gave the tide compound as a white crystalline solid, mp 116–118° C.

Analysis Calc'd for $C_{34}H_{41}N_3O_7$: C, 67.64; H, 6.85; N, 6.96 Found: C, 67.84; H, 6.71; N, 6.92

EXAMPLE 34

8-Aza-spiro[4,5]decane-8-carboxylic acid 6-{[1-(3-phenoxy-phenoxycarbonyl)-piperidine-4-oxycarbonyl]-amino}-hexyl ester A solution of 3-phenoxyphenol (18.3 g, 98 mmol) and pyridine (7.9 ml, 98 mmol) in 300 ml of methylene chloride was added dropwise under nitrogen to a solution of 4-nitrophenyl chloroformate (19.75 g, 98 mmol) in 200 ml of methylene chloride at ice bath temperature. The reaction was stirred at ice bath temperature approximately two hours and then overnight at room temperature. The reaction was extracted one time with 1N HCl, four times with saturated $Na_2CO_3$, dried ($MgSO_4$) and the solvent removed under reduced pressure to give 33.37 g of a brown solid. Five recrystallizations from EtOAc-diisopropyl ether gave 8.6 g (25%) of the desired carbonate as a light tan crystalline solid, mp 105–107° C.

Analysis Calc'd for $C_{19}H_{13}NO_6$: C, 64.96; H, 3.73; N, 3.99 Found: C, 65.12; H, 3.57; N, 4.11

A solution of the carbonate (2.36 g, 6.72 mmol), produced in the preceding step, in 50 ml of methylene chloride was added dropwise under nitrogen to a solution of the amine (HCl salt; 3.0 g, 6.72 mmol), produced in Example 25, and triethylamine (4.68 ml, 33.6 mmol) in 75 ml of methylene chloride at approximately −70° C. The reaction was stirred at −70° C. for 5 hr and dried at room temperature overnight. The reaction was extracted one time with 1N HCl, multiple times with saturated $Na_2CO_3$, dried ($MgSO_4$) and the solvent removed under reduced pressure to give 3.90 g of an oil. Purification of the oil on 400 g of silica gel (230–400 mesh) using hexane-ethyl acetate as the eluent and then recrystallizing the material isolated from hexane gave the title compound (2.53 g, 61%) as a white crystalline solid, mp 72–120° C. (Note: material is a single component by TLC).

Analysis Calc'd for $C_{35}H_{47}N_3O_7$: C, 67.61; H, 7.62; N, 6.76 Found: C, 67.59; H, 7.47; N, 6.79

EXAMPLE 35

8-Aza-spiro[4,5]decane-8-carboxylic acid 6{[1-(4-benzyl-phenoxycarbonyl)-piperidin-4-yl-oxycarbonyl]-amino}-hexyl ester A solution of 4-hydroxydiphenylmethane (20.0 g, 0.11 mol) and pyridine (8.8 ml, 11 mol) in 300 ml of methylene chloride was added dropwise under nitrogen to a solution of 4-nitrophenyl chloroformate (21.88 g, 11 mol) in 200 ml of methylene chloride at ice bath temperature. The reaction was stirred at ice bath temperature for approximately two hours and at room temperature overnight. The reaction was extracted one time with 1N HCl, four times with saturated $Na_2CO_3$, dried ($MgSO_4$) and the solvent removed under reduced pressure to give 37.71 g of a brown crystalline solid. One recrystallization from EtOAc-diisopropyl ether and then repeated recrystallizations from EtOAc gave 17.64 g (47%) of the desired carbonate as a light yellow crystalline solid, mp 100–102°C.

Analysis Calc'd for $C_{20}H_{15}NO_5$: C, 68.77; H, 4.33; N, 4.01 Found: C, 68.65; H, 4.13; N, 3.91

A solution of the carbonate (2.35 g, 6.72 mmol) produced in the previous step in 50 ml of methylene chloride was added dropwise under nitrogen to a solution of the amine (3.0 g, 6.72 mmol; HCl salt) produced in Example 25, and triethylamine (4.68 ml, 33.6 mmol) in 75 ml of methylene chloride at ice bath temperature. After the addition, the reaction was stirred at ice bath temperature for four hours and at room temperature overnight. The reaction was extracted one time with 1N HCl, four times with saturated $Na_2CO_3$, dried ($MgSO_4$) and the solvent removed under reduced pressure to give 3.34 g of a yellow crystalline solid. Chromatography of the solid on 100 g of silica gel (230–400 mesh) using 1:1 EtOAc-hexane as the eluent gave 0.537 g (13%) of the tide compound as a white crystalline solid, mp 78–130° C. (Note: the material is a single component on TLC).

Analysis Calc'd for $C_{30}H_{49}N_3O_6$: C, 69.76; H, 7.97; N, 6.78 Found: C, 69.73; H, 7.83; N, 6.78

EXAMPLE 36

8-Aza-spiro[4,5]decane-8-carboxylic acid 1-[1-(4-phenoxy-phenoxycarbonyl)-piperidin-4-yl-oxycarbonyl]-piperidin-4-yl ester A solution of the carbonate (13.0 g, 27 mmol) produced in Example 3 in 100 ml of methylene chloride was added under nitrogen dropwise to a solution of 4-hydroxypiperidine (3.0 g, 30 mmol) and triethylamine (3.8 ml, 30 mmol) in 100 ml of methylene chloride at approximately −5° C. The reaction was stirred at −5° C. for 2 hours and at room temperature overnight. The reaction was extracted one time with 1N HCl, multiple times with saturated $Na_2CO_3$, dried ($MgSO_4$) and the solvent removed under reduced pressure to give 11.4 g of a white solid. Recrystallization of the solid from ethyl acetate-diisopropyl ether gave the desired alcohol (9.73 g, 81%) as a white crystalline solid, mp 122–123° C.

Analysis Calc'd for $C_{24}H_{28}N_2O_6$: C, 65.44; H, 6.41; N, 6.36 Found: C, 65.46; H, 6.42; N, 6.60

A solution of the alcohol (6.5 g, 14 mmol) produced in the previous step and pyridine (0.93 ml, 11 mmol) in 50 ml of methylene chloride was added dropwise under nitrogen over thirty minutes to a solution of 4-nitrophenyl chloroformate (2.3 g, 11 mmol) in 30 ml of methylene chloride at ice bath temperature. The reaction was stirred at ice bath temperature for two hours and at room temperature overnight. The reaction was extracted one time with 1N HCl, five times with saturated $Na_2CO_3$, dried ($MgSO_4$) and the solvent removed under reduced pressure to give 8.10 g of a white foam. Chromatography of the foam on 400 g of silica gel (230–400 mesh) using 1:1 EtOAc-hexane as the eluent gave 5.56 g (62%) of the desired carbonate as a white crystalline solid, mp 140–142° C.

Analysis Calc'd for $C_{31}H_{31}N_3O_{10}$: C, 61.48; H, 5.16; N, 6.94 Found: C, 61.64; H, 5.18; N, 6.74

A solution of the carbonate (2.0 g, 3.3 mmol) produced in the previous step in 30 ml of anhydrous dimethylformamide was added dropwise under nitrogen to a solution of 8-aza-spiro[4,5]decane-8-carboxylic acid hydrochloride (670 mg, 3.8 mmol) and triethylamine (0.91 ml, 6.6 mmol) in 20 ml of anhydrous dimethylformamide at ice bath temperature. After the addition, the reaction was stirred at ice bath temperature for two hours and at room temperature overnight. The reaction was diluted with ethyl acetate, extracted five times with water, one time with 1N HCl, five times with saturated $Na_2CO_3$, dried ($MgSO_4$) and the solvent removed under reduced pressure to give 1.93 g of a white foam. Chromatography on the foam on 100 g of silica gel (230–400 mesh) using 1:1 EtOAc-hexane as the eluent gave 1.18 g (91%) of the title compound as a white solid foam, mp 48–63° C. (Note: the compound is a single component by TLC).

Analysis Calc'd for $C_{34}H_{43}N_3O_7$: C, 67.42; H, 7.16; N, 6.94 Found: C, 67.05; H, 7.09; N, 6.83

EXAMPLE 37

4-[4-(4-Phenyl-butylcarbamoyloxy)-piperidine-1-carbonyloxy]-piperidine-1-carboxylic acid 4-phenoxyphenyl ester A solution of the carbonate (2.0 g, 3.3 mmol) produced in step 2 of Example 36 in 30 ml of anhydrous dimethylformamide was added dropwise under nitrogen to a solution of 4-phenylbutylamine (0.63 ml, 4.0 mmol) and triethylamine (0.56 ml, 4.0 mmol) in 20 ml of anhydrous dimethylformamide at ice bath temperature. After the addition, the reaction was stirred at ice bath temperature for two hours and overnight at room temperature. The reaction was diluted with ethyl acetate, extracted five times with water, one time with 1N HCl, five times with saturated $Na_2CO_3$, dried ($MgSO_4$), and the solvent removed under reduced pressure to give 2.03 g of a clear oil. Chromatography of the oil on 100 g of silica gel (230–400 mesh) using 10% EtOAc-$CH_2Cl_2$ as the eluent gave 1.72 g (85%) of the title compound as a white solid foam, mp 50–60° C. (Note: the compound is a single component by TLC).

Analysis Calc'd for $C_{35}H_{41}N_3O_7$: C, 68.27; H, 6.71; N, 6.82 Found: C, 67.87; H, 6.69; N, 6.76

EXAMPLE 38

4-(4-Hexylcarbamoyl-cyclohexylcarbamoyloxy)-piperidine-1-carboxylic acid 4-phenoxyphenyl ester A solution of the carbonate (10.0 g, 21 mmol), produced in Example 3, in 100 ml of anhydrous dimethylformamide was added dropwise under nitrogen to a solution of trans-4-aminocyclohexanol hydrochloride (3.5 g, 23 mmol) and triethylamine (6.4 ml, 46 mmol) in 50 ml of anhydrous dimethylformamide at ice bath temperture. After the addition, the reaction was stirred at ice bath temperature for two hours and overnight at room temperature. The reaction was diluted with ethyl acetate, extracted five times with water, one time with 1N HCl, five times with saturated $Na_2CO_3$, dried ($MgSO_4$) and the solvent removed under reduced pressure to give 8.39 g of a white solid. Recrystallization of the solid from EtOAc-hexane gave 6.45 g (68%) of the desired alcohol as a white crystalline solid, mp 155–156° C.

Analysis Calc'd for $C_{25}H_{30}N_2O_6$: C, 66.06; H, 6.65; N, 6.16 Found: C, 66.08; H, 6.67; N, 6.01

A solution of the alcohol (2.0 g, 4.4 mmol) produced in the previous step, triethylamine (0.49 ml, 3.5 mmol) and hexyl isocyanate (1.2 g, 9.7 mmol) in 20 ml of chloroform (EtOH free) was refluxed under nitrogen until the reaction was complete by TLC. The reaction was extracted two times with 1N HCl, dried ($MgSO_4$) and the solvent removed under reduced pressure to give 2.80 g of a white solid. Recrystallization of the solid from ethyl acetate gave 2.06 g (81%) of the title compound as a white crystalline solid, mp 190–191° C.

Analysis Calc'd for $C_{32}H_{43}N_3O_7$: C, 66.07; H, 7.45; N, 7.22 Found: C, 66.10; H, 7.50; N, 7.27

EXAMPLE 39

4-[6-(Hexylcarbamoyloxy)-hexylcarbamoyloxy]-piperidine-1-carboxylic acid 4-cyclohexyl-phenyl ester A solution of 4-cyclohexylphenol (20.0 g, 0.11 mol) and pyridine (9.2 ml, 0.11 mol) in 300 ml of methylene chloride was added dropwise under nitrogen to a solution of 4-nitrophenyl chloroformate (22.88 g, 11 mmol) in 200 ml of methylene chloride at ice bath temperature. The reaction was stirred at ice bath temperature for approximately two hours and at room temperature overnight. The reaction was extracted one time with 1N HCl, four times with saturated $Na_2CO_3$, dried ($MgSO_4$) and the solvent removed under reduced pressure to give 37.23 g of a yellow solid. Chromatography of the solid on 500 g of silica gel (230–400 mesh) using 40% $CH_2Cl_2$-hexane as the eluent and then recrystallization of the material isolated from diisopropyl ether gave 18.9 g (49%) of the desired carbonate as a whtie solid, mp 93–94° C.

Analysis Calc'd for $C_{19}H_{19}NO_5$: C, 66.85; H, 5.61; N, 4.10 Found: C, 66.85; H, 5.56; N, 4.16

A solution of the carbonate (2.76 g, 8.08 mmol) produced in the previous step in 50 ml of methylene chloride was added dropwise under nitrogen to a solution of (6-hexylcarbamoyloxy-hexyl)carbamic acid piperidin-4-yl ester (3.0 g, 8.08 mmol) and triethylamine (3.38 ml, 24.2 mmol) in 75 ml of methylene chloride at ice bath temperature. After the addition, the reaction was stirred at ice bath temperature for 3 hours and overnight at room temperature. The reaction was extracted one time with 1N HCl, four times with saturated $Na_2CO_3$, dried ($MgSO_4$) and the solvent removed under reduced pressure to give 4.27 g of a solid. Recrystallization of the solid from EtOAc-diisopropyl ether gave 2.69 g (58%) of the title compound as a white crystalline compound, mp 94–96° C.

Analysis Calc'd for $C_{32}H_{51}N_3O_6$: C, 66.99; H, 8.96; N, 7.32 Found: C, 66.70; H, 8.96; N, 7.36

EXAMPLE 40

8-Aza-spiro[4,5]decane-8-carboxylic acid 4-{[1-(4-phenoxy-phenoxycarbonyl)-piperidine-4-carbonyl]amino}-cyclohexyl ester A solution of the alcohol (3.30 g, 7.3 mmol) produced in step 1 of Example 38 and pyridine (0.59 ml, 7.3 mmol) in 50 ml of methylene chloride was added dropwise under nitrogen to a solution of 4-nitrophenyl chloroformate (1.5 g, 7.3 mmol) in 30 ml of methylene chloride at ice bath temperature. The reaction was stirred at ice bath temperature for 2 hours and then overnight at room temperature. The reaction was extracted one time with 1N HCl, five times with saturated $Na_2CO_3$, dried ($MgSO_4$) and the solvent removed under reduced pressure to give 4.42 g of an off-white solid. Recrystallization of the solid from EtOAc-diisopropyl ether gave 2.36 g (52%) of the desired carbonate as a white crystalline solid, mp 152–155° C.

Analysis Calc'd for $C_{32}H_{33}N_3O_{10}$: C, 62.03; H, 5.37; N, 6.78 Found: C, 62.42; H, 5.45; N, 6.78

A solution of the carbonate (2.0 g, 3.2 mmol) produced in the previous step in 30 ml of anhydrous dimethylformamide was added dropwise under nitrogen to a solution of 8-aza-spiro-[4,5]-decane-8-carboxylic acid hydrochloride (680 mg, 3.9 mmol) and triethylamine (1.0 ml, 7.1 mmol) in 20 ml of anhydrous dimethylformamide at ice bath temperature. After the addition, the reaction was stirred at ice bath temperature for two hours and overnight at room temperature. The reaction was diluted with ethyl acetate, extracted five times with water, one time with 1N HCl, five times with saturated $Na_2CO_3$, dried ($MgSO_4$) and the solvent removed under reduced pressure to give 2.12 g of an off-white solid. Recrystallization of the solid from EtOAc gave 1.42 g (71%) of the title compound as a white crystalline solid, mp 230–231° C.

Analysis Calc'd for $C_{35}H_{45}N_3O_7$: C, 67.83; H, 7.32; N, 6.78 Found: C, 67.74; H, 7.36; N, 6.74

EXAMPLE 41

4-(4-Hexylcarbamoyl-piperidine-1-carbonyloxy]-piperidine-1-carboxylic acid 4-phenoxyphenyl ester A solution of the alcohol (2.0 g, 4.54 mmol) produced in step 1 of Example 36, triethylamine (0.51 ml, 3.36 mmol) and hexyl isocyanate (690 mg, 5.45 mmol) in 20 ml of $CHCl_3$ (EtOH free) was refluxed under nitrogen for approximately 24 hours. An additional 580 mg (4.56 mmol) of hexyl isocyanate was added and the reaction refluxed for 6 hours and at room temperature for 48 hours. One more equivalent of hexyl isocyanate was added and the reaction refluxed for approximately 24 hours. The reaction was extracted two times with 1N HCl, dried ($MgSO_4$) and the solvent removed under reduced pressure to give 2.92 g of a clear oil. Purification of the oil by chromatography on silica gel (230–400 mesh) using 1:1 EtOAc-hexane as the eluent gave 1.98 g (77%) of the tide compound as a clear oil, MS m/e 567 (M+).

Analysis Calc'd for $C_{31}H_{41}N_3O_7$: C, 65.59; H, 7.28; N, 7.40 Found: C, 65.05; H, 7.40; N, 7.44

EXAMPLE 42

4-{4-[(Hexylcarbamoyloxy)methyl]-(cyclohexylmethylcarbamoyl)oxy}-piperidine-1-carboxylic acid 4-phenoxyphenyl ester A solution of the carbonate (1.95 g, 4.1 mmol) produced in Example 3 in 20 ml of anhydrous dimethylformamide was added dropwise under nitrogen to a solution of 4-(aminomethyl)-cyclohexanemethanol (700 mg, 4.9 mmol) and triethylamine (0.68 ml, 4.9 mmol) in 10 ml of anhydrous dimethylformamide at ice bath temperature. The reaction was stirred at ice bath temperature for approximately two hours and at room temperature overnight. The reaction was diluted with ethyl acetate, extracted five times with water, one time with 1N HCl, five times with saturated $Na_2CO_3$, dried ($MgSO_4$) and the solvent removed under reduced pressure to give 1.89 g of a yellow oil. Chromatography on the oil on 200 g of silica gel (230–400 mesh) using 20% EtOAc-$CH_2Cl_2$ as the eluent gave 775 mg (39%) of the desired alcohol as a white crystalline solid, mp 97–110° C. (Note: the compound is a single component by TLC).

Analysis Calc'd for $C_{27}H_{34}N_2O_6$6: C, 67.20; H, 7.10; N, 5.81 Found: C, 66.92; H, 7.09; N, 5.76

A solution of the alcohol (700 mg, 1.45 mmol) produced in the previous step, triethylamine (0.16 ml, 1.16 mmol) and hexyl isocyanate (406 mg, 3.19 mmol) in 10 ml of $CHCl_3$ (EtOH free) was refluxed under nitrogen for 55 hours. The reaction was extracted two times with 1N HCl, dried ($MgSO_4$) and the solvent removed under reduced pressure to give 987 mg of an off-white solid. Recrystallization of the solid from EtOAc-diisopropyl ether gave 642 mg (73%) of the title compound as a white crystalline solid, mp 99–102° C.

Analysis Calc'd for $C_{34}H_{47}N_3O_7$: C, 66.97; H, 7.77; N, 6.89 Found: C, 66.91; H, 7.74; N, 7.05

In-Vitro and In-Vivo Pharmacological Procedures

1. The ability of the compounds of this invention to inhibit acyl-coenzyme A: cholesterol acyltransferase was established by initially showing that they inhibited intracellular cholesterol esterification by subjecting them to the standard experimental test procedure of Ross et al., J. Biol. Chem. 259, 814 (1984). The results are reported in the following table, where available, in terms of the percent inhibition at 25 $\mu$M and the $IC_{50}$ ($\mu$M).

2. The ability of the compounds of this invention to inhibit the formation of cholesteryl esters and thereby interfere with and prevent assimilation of cholesterol into the lymphatic system and ultimately the blood stream was established by incubating the compounds at 37C. with a mixture of cholesterol and oleic acid in the presence of buffered cholesterol esterase [(EC 3.1.1.13) Sigma Company, St. Louis, Mo., U.S.A., No. C-1892, from bovine pancreas] and measuring the amount of ester formed, according to the procedure of Field. J. of Lipid Research, 25, 389 (1984). The concentration of test compound that inhibits one-half of the ester formation ($IC_{50}$ $\mu$M) is given in the following table.

The in vivo cholesterol absorption studies were conducted in normal rats by oral administration of the compound being tested in propylene glycol and olive oil followed by oral administration of [4-$^{14}$C] cholesterol in propylene glycol and olive oil, otherwise following the procedure of Cayen et al., J. Lipid Res. 20 162 (1979). The serum radioactivity was measured at six hours after dosing. The results of this study are reported in the following table as percent decrease compared to control at the dose stated.

TABLE

| Examples | In Vitro Results % inhibition at 25 $\mu$M/$IC_{50}$ ($\mu$M) | | In Vivo Results Effect on Absorption of $^{14}$C-chol.-6 hr-normal |
|---|---|---|---|
| Compound | ACAT | CEH | % Decrease (dose mg/kg) |
| 6 | 97%/1.78 | 0.42 | 59% (3) |
| 7 | 76%/6.41 | 0.67 | 42% (20) |
| 8 | 98%/2.34 | 0.54 | 65% (3) |
| 9 | 95%/1.59 | 0.08 | 49% (10) |
| 10 | 83%/5.0 | 0.62 | 22% (20) |
| 11 | 24% | 28.2 | 6% (20) |
| 12 | 83%/1.72 | 0.31 | 76% (10) |
| 13 | 47% | 15.5 | 20% (20) |
| 14 | 41% | >100 | 2% (20) |
| 16 | NT | 0.73 | 68% (10) |
| 18 | NT | 0.51 | 50% (10) |

Thus, the representative compounds of this invention reduce absorption of cholesterol into the blood and thus can be used in the treatment of atherosclerosis, familial hypercholesterolemia, hyperlipidemia and like diseases where a reduction in cholesterol absorption is desired. The dosage requirement for therapeutic use of the antihypercholesterolemic agents of this invention will vary according to the particular compound chosen as well as the age of the patient and severity and nature of the disease being treated. Therapy should be initiated at lower doses, the dosage thereafter being increased, if necessary, to produce the desired effect. In general, the compounds of this invention are most desirably administered at a concentration that will generally afford effective results without causing any harmful or deleterious side effects. Based upon the in vivo potency of the representative anticholesterolemic agents of this invention as reported in the table, the initial dosing will be from about 0.5 to 6 mg/kg with a projected maximum dose of about 100 mg/kg. The preferred dosage range will be from about 1 to 50 mg/kg.

The compounds of formula (I) can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be sufficient at last to impart the desired activity thereto on oral administration. The compounds may also be injected parenterally in which case they are used in the form of a sterile solution containing other solutes, for example, enough saline or glucose to make the solution isotonic.

What is claimed is:

1. A compound having the formula:

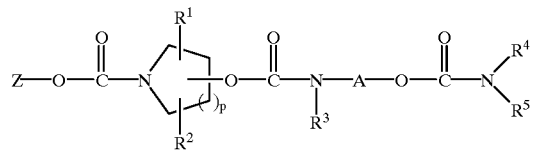

wherein p is 0, 1, 2, 3, or 4;

Z is —$Ar^1$, —$Ar^1$—$Ar^2$, —$Ar^1$—O—$Ar^2$, —$Ar^1$—S—$Ar^2$,

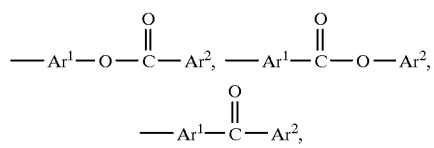

—$Ar^1$—$(CH_2)_{1-20}$—$Ar^2$, —$Ar^1$—O—$(CH_2)_{1-20}$—O—$Ar^2$, —$Ar^1$—O—$(CH_2)_{1-20}$—$Ar^2$, —$Ar^1(CR^6$=$CR^6)_{1-3}$—$Ar^2$, or —$Ar^1$—$NR^7$—$Ar^2$; where $R^6$ is hydrogen or $C_1$–$C_8$ alkyl; and $R^7$ is hydrogen, $C_1$–$C_8$ alkyl, $C_1$–$C_8$ alkylcarbonyl, or $C_1$–$C_8$ alkoxycarbonyl; and $Ar^1$ and $Ar^2$ are, independently, selected from phenyl, naphthyl, indenyl, fluorenyl, furanyl, benzofuranyl, dibenzofuranyl, thienyl, benzothienyl, pyridinyl, indolyl, quinolinyl, isoquinolinyl, carbazolyl, pyrimidinyl, pyrazinyl, imidazolyl, benzimidazolyl, benzotriazolyl, oxazolyl, benzoxazolyl, isoxazolyl, benzisoxazolyl, or thiazolyl, benzthiazolyl; and $Ar^1$ and $Ar^2$, independently, are optionally substituted by fluorine, chlorine, bromine, iodine, cyano, nitro, —$CO_2H$, $C_1$–$C_{20}$ alkyl, $C_2$–$C_{20}$ alkenyl, $C_3$–$C_8$ cycloalkyl, $C_1$–$C_{20}$ alkoxy, $C_1$–$C_{20}$ alkyl-O—($C_1$–$C_{20}$ alkyl)—, $C_1$–$C_{20}$ alkyl-O—($C_1$–$C_{20}$-alkyl)—O—, trifluoromethyl, $C_1$–$C_{20}$ alkylcarbonyl, $C_3$–$C_8$ cycloalkyloxy, $C_1$–$C_{20}$ alkylcarbonyloxy, $C_1$–$C_{20}$ alkoxycarbonyl, mono or di $C_1-C_{20}$ alkylaminocarbonyl, tetrazolyl, —OH, —SH, —$(CH_2)_{1-}$—OH, —$NH_2$, or —$(CH_2)_{1-6}$—$NR^8R^9$; where $R^8$ is $C_1-C_{20}$ alkyl, $C_1-C_{20}$ alkylcarbonyl, $C_1-C_{20}$ alkoxycarbonyl; and $R^9$ is hydrogen or $C_1-C_{20}$ alkyl; or $R^8$ and $R^9$ together with the nitrogen atom to which they are attached form a heterocyclic ring of the formula:

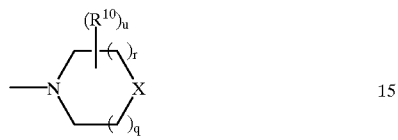

where q is 0, 1 or 2; r is 1 or 2; and u is 0, 1 or 2;
$R^{10}$ is $C_1-C_8$ alkyl; and
X is —O—, —S—, —$NR^{11}$— or —$CR^{12}R^{13}$—; where $R^{11}$ is H, $C_1-C_{20}$ alkyl or benzyl;

$R^{12}$ is H, OH, $C_1-C_{20}$ alkyl, $C_1-C_{20}$ alkoxy, $C_1-C_{20}$ alkylcarbonyloxy, $Ar^1$, or —$(CH_2)_{1-10}$—$Ar^1$;

$R^{13}$ is H or $C_1-C_{20}$ alkyl; or $R^{12}$ and $R^{13}$ together with the carbon atom to which they are attached form a 3 to 8 membered carbocyclic ring;

A is a bridging group selected from:
(1) a saturated or unsaturated, straight or branched hydrocarbon chain of 1 to 20 carbon atoms and which may have 1 to 6 sites of olefinic and/or acetylenic unsaturation;
(2) a group of the formula: —$(CH_2)_m$—W—$(CH_2)_n$—, where m and n are 1 to 19, m plus n is 2 to 20; and W is a group selected from —O—, —S— or $NR^{14}$; where
$R^{14}$ is hydrogen, $C_1-C_{20}$ alkyl, $C_1-C_{20}$ alkylcarbonyl, $C_1-C_{20}$ alkoxycarbonyl or benzyl;
(3) a group of the formula:

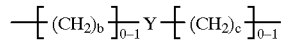

where b and c are, independently, 1 to 20, and b plus c is 1 to 20, and Y is selected from the group consisting of:

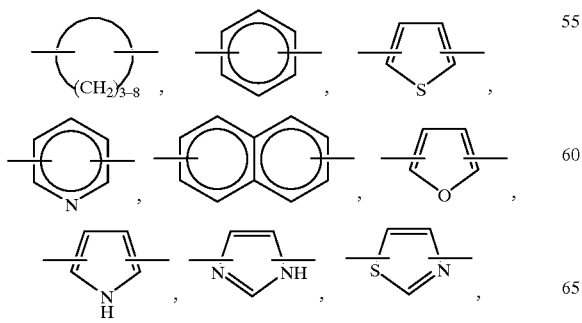

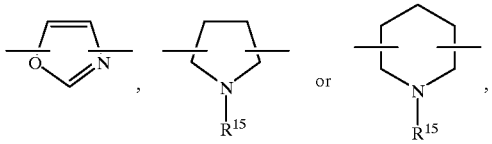

where $R^{15}$ is H, $C_1-C_8$ alkyl, $C_1-C_{20}$ alkylcarbonyl, $C_1-C_{20}$ alkoxycarbonyl, or benzyl; or A together with $R^3$ and the nitrogen atom to which they are attached form a heterocyclic moiety of the formula:

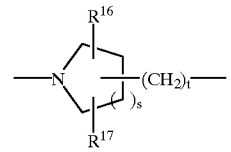

where s is 0, 1, 2, 3 or 4; t is 0 to 15; and $R^{16}$ and $R^{17}$ are, independently, hydrogen, $C_1-C_8$ alkyl, $C_1-C_8$ alkoxy, $C_1-C_8$ alkylcarbonyl, hydroxy, cyano, $C_1-C_8$ alkylcarbonyloxy, or —$(CH_2)_{0-6}$—$NR^{18}R^{19}$; where $R^{18}$ is $C_1-C_8$ alkyl, $C_1-C_8$ alkoxycarbonyl, or $C_1-C_8$ alkylcarbonyl; and $R^{19}$ is hydrogen or $C_1-C_8$ alkyl;

$R^1$ and $R^2$ are independently hydrogen, $C_1-C_8$ alkyl, $C_1-C_8$ alkoxy, $C_1-C_8$ alkylcarbonyl, hydroxy, cyano, $C_1-C_8$ alkylcarbonyloxy, or —$(CH_2)_{0-6}$—$NR^{18}R^{19}$; where $R^{18}$ is $C_1-C_8$ alkyl, $C_1-C_8$ alkoxycarbonyl, or $C_1-C_8$ alkylcarbonyl; and $R^{19}$ is —H or $C_1-C_8$ alkyl;

$R^3$ is H, $C_1-C_8$ alkyl or $C_7-C_{15}$ arylalkyl where aryl is phenyl optionally substituted with a $C_1-C_6$ alkyl group; or $R^3$ is combined with A to form a heterocyclic ring as described above;

$R^4$ and $R^5$ are independently hydrogen, $C_1-C_{20}$ alkyl, $C_2-C_{20}$ alkenyl, $C_3-C_{10}$ cycloalkyl, cycloalkylalkyl having 3–10 carbon atoms in the cycloalkyl moiety and 1–20 carbon atoms in the alkyl moiety, —$(CH_2)_{1-20}Ar^1$ or —$(CH_2)_{1-20}NR^2OR^{21}$; where $R^{20}$ is $C_1-C_{20}$ alkyl, $C_2-C_{20}$ alkenyl, $C_1-C_{20}$ alkylcarbonyl, $C_1-C_{20}$ alkoxycarbonyl or benzyl; and $R^{21}$ is hydrogen or $C_1-C_{20}$ alkyl; or $R^4$ and $R^5$ together with the nitrogen atom to which they are attached form a heterocyclic moiety of the formula:

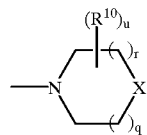

where r, q, u, $R^{10}$ and X are as defined above, or a pharmaceutically acceptable salt thereof.

2. A compound according to claim 1 wherein

Z is —$Ar^1$, —$Ar^1$—$Ar^2$, —$Ar^1$—O—$Ar^2$, —$Ar^1$—S—$Ar^2$, $$-Ar^1-O-\overset{O}{\underset{\|}{C}}-Ar^2, \quad -Ar^1-\overset{O}{\underset{\|}{C}}-O-Ar^2,$$

$$-Ar^1-\overset{O}{\underset{\|}{C}}-Ar^2,$$

—$Ar^1$—$(CH_2)_{1-20}$—$Ar^2$, —$Ar^1$—$(CH_2)_{1-20}$—O—$Ar^2$, —$Ar^1$—O—$(CH_2)_{1-20}$—$Ar^2$, —$Ar^1$—$(CR^6=CR^6)_{1-3}$—$Ar^2$ or —$Ar^1$—$NR^7$—$Ar^2$;

$R^6$ is H or $C_1$–$C_8$ alkyl;

$R^7$ is hydrogen, $C_1$–$C_8$ alkyl, $C_1$–$C_8$ alkylcarbonyl or $C_1$–$C_8$ alkoxycarbonyl; and $Ar^1$ and $Ar^2$ are selected from phenyl, naphthyl, indenyl, fluorenyl, furanyl, benzofuranyl, dibenzofuranyl, thienyl, benzothienyl, pyridinyl, indolyl, quinolinyl, isoquinolinyl, carbazolyl, imidazolyl, benzimidazolyl, oxazolyl, benzoxazolyl, isoxazolyl, benzisoxazolyl, or thiazolyl, benzthiazolyl; and $Ar^1$ and $Ar^2$ may be optionally substituted by fluorine, chlorine, bromine, iodine, cyano, nitro, —$CO_2H$, $C_1$–$C_8$ alkyl, $C_1$–$C_8$ alkoxy, $C_2$–$C_8$ alkenyl, trifluoromethyl, $C_3$–$C_8$ cycloalkyl, $C_3$–$C_8$ cycloalkyloxy, $C_1$–$C_8$ alkylcarbonyl, $C_1$–$C_8$ alkoxycarbonyl, $C_1$–$C_8$ alkylcarbonyloxy, —$NH_2$, —$(CH_2)_{1-6}$—$NR^8R^9$; where $R^8$ is $C_1$–$C_8$ alkyl, $C_1$–$C_8$ alkylcarbonyl or $C_1$–$C_8$ alkoxycarbonyl; and $R^9$ is hydrogen or $C_1$–$C_8$ alkyl.

3. A compound according to claim 1 wherein

A is a bridging group selected from:
(1) a saturated or unsaturated, straight or branched hydrocarbon chain of 1 to 20 carbon atoms which may have 1 to 6 sites of olefinic and/or acetylenic unsaturation;
(2) a group of the formula —$(CH_2)_m$—W—$(CH_2)_n$—, where m and n are 1 to 19, m+n is 2 to 20; and W is a group selected from —O—, —S—, or —$NR^{14}$—; where
$R^{14}$ is hydrogen, $C_1$–$C_8$ alkyl, $C_1$–$C_8$ alkylcarbonyl, $C_1$–$C_8$ alkoxycarbonyl or benzyl;
(3) a group of the formula:

$$-[(CH_2)_b]_{0-1}-Y-[(CH_2)_c]_{0-1}-$$

where b and c are 1 to 20, b+c is 1 to 20, and Y is selected from the group consisting of:

phenyl, $(CH_2)_{3-8}$ bridged cyclohexyl, pyridinyl, or thienyl;

or A together with $R^3$ and the interposed nitrogen form a heterocyclic moiety of the formula:

$$-N\underset{)_s}{\overset{}{\diagdown}}(CH_2)_t-$$

where s is 0, 1, 2 or 3; and t is 0 to 15.

4. A compound according to claim 1 wherein $R^4$ and $R^5$ are, independently, hydrogen, $C_1$–$C_{12}$ alkyl, $C_2$–$C_8$ alkenyl, $C_3$–$C_8$ cycloalkyl, —$(CH_2)_{1-10}$—($C_3$–$C_{10}$ cycloalkyl), —$(CH_2)_{1-10}Ar^1$, —$(CH_2)_{1-10}$—$NR^{20}R^{21}$; where $R^{20}$ is $C_1$–$C_8$ alkyl, $C_2$–$C_8$ alkenyl, $C_1$–$C_8$ alkylcarbonyl, $C_1$–$C_8$ alkoxycarbonyl or benzyl; and $R^{21}$ is hydrogen or $C_1$–$C_8$ alkyl; or $R^4$ and $R^5$ together with the interposed nitrogen forms a heterocyclic moiety of the formula:

[heterocyclic structure with $(R^{10})_u$, $(\ )_r$, $(\ )_q$, N, and X]

where q is 0, 1 or 2; r is 1 or 2; u is 0, 1 or 2;

$R^{10}$ is $C_1$–$C_8$ alkyl; and

X is —O—, —S—, —$NR^{11}$— or $CR^{12}R^{13}$; where $R^{11}$ is hydrogen, $C_1$–$C_8$ alkyl or benzyl;

$R^{12}$ is hydrogen, hydroxy, $C_1$–$C_8$ alkyl, $C_1$–$C_8$ alkoxy; and $R^{13}$ is hydrogen or $C_1$–$C_8$ alkyl; or $R^{12}$ and $R^{13}$ together with the interposed carbon forms a 3 to 8 membered carbocyclic ring.

5. A compound according to claim 1 having the formula:

$$Z-O-\overset{O}{\underset{\|}{C}}-N\diagup\diagdown-O-\overset{O}{\underset{\|}{C}}-\underset{R^3}{N}-A-O-\overset{O}{\underset{\|}{C}}-N\diagdown_{R^5}^{R^4}$$

in which Z, $R^3$, $R^4$ and $R^5$ are defined in claim 1 or a pharmaceutically acceptable salt thereof.

6. A compound according to claim 1 having the formula:

$$Z-O-\overset{O}{\underset{\|}{C}}-N\diagup\diagdown-O-\overset{O}{\underset{\|}{C}}-\underset{R^3}{N}-A-O-\overset{O}{\underset{\|}{C}}-N\diagdown_{R^5}^{R^4}$$

in which Z, $R^3$, $R^4$ and $R^5$ are defined in claim 1 or a pharmaceutically acceptable salt thereof.

7. A compound according to claim 1 wherein $Ar^1$ is phenyl or naphthyl.

8. A compound according to claim 1 wherein Z is 4-phenoxyphenyl.

9. A compound according to claim 8 which is 4-[6-(hexylcarbamoyloxy)hexylcarbamoyl-oxy]-piperidine-1-carboxylic acid 4-phenoxyphenyl ester, or a pharmaceutically acceptable salt thereof.

10. A compound according to claim 8 which is 8-azaspiro[4,5]decane-8-carboxylic acid 6-{[1-(4-phenoxyphenoxycarbonyl)-piperidine-4-oxycarbonyl]amino}hexyl ester, or a pharmaceutically acceptable salt thereof.

11. A compound according to claim 1 selected from the group consisting of:

4-[6-(dihexyl-carbamoyloxy)-hexylcarbamoyloxy]-piperidine-1-carboxylic acid 4-phenoxyphenyl ester, 4-[6-(piperidine-1-carbonyloxy)-hexylcarbamoyloxy]-piperidine-1-carboxylic acid 4-phenoxyphenyl ester, 4-[6-dibenzyl-carbamoyloxy)-hexyl-carbamoyloxy]-piperidine-1-carboxylic acid 4-phenoxyphenyl ester, 4-[12-(hexylcarbamoyloxy)-dodecylcarbamoyloxy]-piperidine-1-carboxylic acid 4-phenoxyphenyl ester, 4-{6-[4-(2,2-dimethyl-propyl)-benzyl)-heptyl-carbamoyloxy]-hexyl-carbamoyloxy}-piperidine-1-carboxylic acid 4-phenoxyphenyl ester, (Z)-4-[6-(octadec-9-enylcarbamoyloxy)-hexylcarbamoyloxy]-piperidine-1-carboxylic acid 4-phenoxyphenyl ester, (Z)-4-[12-(octadec-9-enylcarbamoyloxy)-dodecylcarbamoyloxy]-piperidine-1carboxylic acid 4-phenoxyphenyl ester, 4-[6-(hexylcarbamoyloxy)-propylcarbamoyloxy]-piperidine-1-carboxylic acid 4-phenoxyphenyl ester, 4-[9-(nonylcarbamoyloxy)-propylcarbamoyloxy]-piperidine-1-carboxylic acid 4-phenoxyphenyl ester, 8-aza-spiro[4,5]decane-8-carboxyolic acid 6-{[1-(4-phenoxy-phenoxycarbonyl)-piperidine-4-oxycarbonyl]-amino}-propyl ester, 8-aza-spiro[4,5]decane-8-carboxylic acid 6-{[1-(4-nitro-phenoxycarbonyl)-piperidine-4-oxycarbonyl]-amino}hexyl ester, 8-aza-spiro[4,5]decane-8-carboxylic acid 6-{[1-(dibenzofuran-2-yloxycarbonyl)piperidine-4-yl]-oxycarbonylamino}-hexyl ester, 8-aza-spiro[4,5]decane-8-carboxylic acid 6-{[1-(4-phenyl-phenoxycarbonyl)-piperidine-4-oxycarbonyl]-amino}-hexyl ester, 8-aza-spiro[4,5]decane-8-carboxylic acid 6-{[1-(4-pentyl-phenoxycarbonyl)-piperidine-4-oxycarbonyl]-amino}-hexyl ester, 4-[4-(Hexylcarbamoyloxymethyl)-benzylcarbamoyloxy]-piperidine-1-carboxylic acid 4-phenoxyphenyl ester, 8-Aza-spiro[4,5]decane-8-carboxylic acid 6-{[1-(3-phenoxy-phenoxycarbonyl)-piperidine-4-oxycarbonyl]-amino}-hexyl ester, 8-Aza-spiro[4,5]decane-8-carboxylic acid 6-{[1-(4-benzyl-phenoxycarbonyl)-piperidin-4-yl]-oxycarbonyl]-amino}-hexyl ester, 8-Aza-spiro[4,5]decane-8-carboxylic acid 1-[1-(4-phenoxy-phenoxycarbonyl)-piperidin-4-yl-oxycarbonyl]-piperidin-4-yl ester, 4-[4-(4-Phenyl-butylcarbamoyloxy)-piperidine-1-carbonyloxy]-piperidine-1-carboxylic acid 4phenoxyphenyl ester, 4(4-Hexylcarbamoyl-cyclohexylcarbamoyloxy)-piperidine-1-carboxylic acid 4-phenoxyphenyl ester, 4-[6-(Hexylcarbamoyloxy)-hexylcarbamoyloxy]-piperidine-1-carboxylic acid 4-cyclohexyl-phenyl ester, 8-Aza-spiro[4,5]decane-8-carboxylic acid 4-{[1-(4-phenoxy-phenoxycarbonyl)-piperidine-4-carbonyl]amino}-cyclohexyl ester, 4-(4-Hexylcarbamoyl-piperidine-1-carbonyloxy]-piperidine-1-carboxylic acid 4-phenoxyphenyl ester, and 4-{4-[(Hexylcarbamoyloxy)methyl]-(cyclohexylmethylcarbamoyl)oxy}piperidine-1-carboxylic acid 4-phenoxyphenyl ester.

12. A compound having the formula:

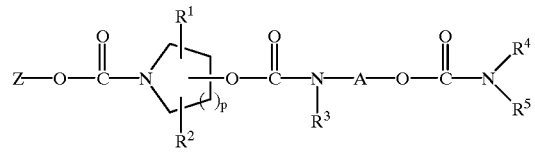

wherein p is 2;

Z is —Ar$^1$, —Ar$^1$—Ar$^2$, —Ar$^1$—O—Ar$^2$, or —Ar$^1$—S—Ar$^2$;

Ar$^1$ and Ar$^2$ are, independently, selected from phenyl and naphthyl;

Ar$^1$ and Ar$^2$, independently, are optionally substituted by fluorine, chlorine, bromine, iodine, cyano, nitro, $C_1$–$C_{20}$ alkyl, $C_2$–$C_{20}$ alkenyl, $C_3$–$C_8$ cycloalkyl, $C_1$–$C_{20}$ alkoxy, $C_1$–$C_{20}$ alkyl-O—($C_1$–$C_{20}$ alkyl)—, $C_1$–$C_{20}$ alkyl-O—($C_1$–$C_{20}$-alkyl)—O—, trifluoromethyl, $C_1$–$C_{20}$ alkylcarbonyl, $C_3$–$C_8$ cycloalkyloxy, —OH, —SH, —($CH_2$)$_{1-6}$—OH, —NH$_2$, or —($CH_2$)$_{1-6}$NR$^8$R$^9$; where R$^8$ is $C_1$–$C_{20}$ alkyl, and R$^9$ is hydrogen or $C_1$–$C_{20}$ alkyl;

A is a bridging group selected from a saturated or unsaturated, straight or branched hydrocarbon chain of 1 to 20 carbon atoms and which may have 1 to 6 sites of olefinic and/or acetylenic unsaturation;

R$^1$ and R$^2$ are independently hydrogen, $C_1$–$C_8$ alkyl, $C_1$–$C_8$ alkoxy, $C_1$–$C_8$ alkylcarbonyl, hydroxy, or cyano;

R$^3$ is H, $C_1$–$C_8$ alkyl or $C_7$–$C_{15}$ arylalkyl where aryl is phenyl optionally substituted with a $C_1$–$C_6$ alkyl group;

R$^4$ and R$^5$ are independently hydrogen, $C_1$–$C_{20}$ alkyl, $C_2$–$C_{20}$ alkenyl, $C_3$–$C_{10}$ cycloalkyl, or cycloalylalkyl having 3–10 carbon atoms in the cycloalkyl moiety and 1–20 carbon atoms in the alkyl moiety, or a pharmaceutically acceptable salt thereof.

13. A compound having the formula:

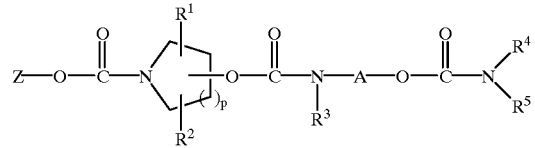

wherein p is 0, 1, 2, 3, or 4;

Z is —Ar$^1$, —Ar$^1$—Ar$^2$, —Ar$^1$—O—Ar$^2$, —Ar$^1$—S—Ar$^2$,

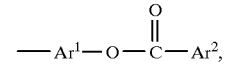

—Ar$^1$—($CH_2$)$_{1-20}$—Ar$^2$, —Ar$^1$—($CH_2$)$_{1-20}$—O—Ar$^2$, —Ar$^1$—O—($CH_2$)$_{1-20}$—Ar$^2$, —Ar$^1$—(CR$^6$=CR$^6$)$_{1-3}$—Ar$^2$, or —Ar$^1$—NR$^7$—Ar$^2$; where $R^6$ is hydrogen or $C_1$–$C_8$ alkyl; and $R^7$ is hydrogen, $C_1$–$C_8$ alkyl, $C_1$–$C_8$ alkylcarbonyl, or $C_1$–$C_8$ alkoxycarbonyl; and $Ar^1$ and $Ar^2$ are, independently, selected from phenyl, naphthyl, indenyl, fluorenyl, and $Ar^1$ and $Ar^2$, independently, are optionally substituted by fluorine, chlorine, bromine, iodine, cyano, nitro, —$CO_2H$, $C_1$–$C_{20}$ alkyl, $C_2$–$C_{20}$ alkenyl, $C_3$–$C_8$ cycloalkyl, $C_1$–$C_{20}$ alkoxy, $C_1$–$C_{20}$ alkyl-O—($C_1$–$C_{20}$ alkyl)—, $C_1$–$C_{20}$ alkyl-O—($C_1$–$C_{20}$ alkyl)—O—, trifluoromethyl, $C_1$–$C_{20}$ alkylcarbonyl, $C_3$–$C_8$ cycloalkyloxy, $C_1$–$C_{20}$ alkylcarbonyloxy, $C_1$–$C_{20}$ alkoxycarbonyl, mono or di $C_1$–$C_{20}$ alkylaminocarboyl, tetrazolyl, —OH, —SH, —($CH_2$)$_{1-6}$—OH, —$NH_2$, or —($CH_2$)$_{1-6}$—$NR^8R^9$; where $R^8$ is $C_1$–$C_{20}$ alkyl, $C_1$–$C_{20}$ alkylcarbonyl, $C_1$–$C_{20}$ alkoxycarbonyl; and $R^9$ is hydrogen or $C_1$–$C_{20}$ alkyl;

A is a bridging group selected from:
(1) a saturated or unsaturated, straight or branched hydrocarbon chain of 1 to 20 carbon atoms and which may have 1 to 6 sites of olefinic and/or acetylenic unsaturation;
(2) a group of the formula: —($CH_2$)$_m$—W—($CH_2$)$_n$—, where m and n are 1 to 19, m plus n is 2 to 20, and W is a group selected from —O—, —S— or —$NR^{14}$—; where
$R^{14}$ is hydrogen, $C_1$–$C_{20}$ alkyl, $C_1$–$C_{20}$ alkylcarbonyl, $C_1$–$C_{20}$ alkoxycarbonyl or benzyl;
(3) a group of the formula:

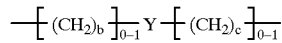

where b and c are, independently, 1 to 20, and b plus c is 1 to 20, and Y is selected from the group consisting of:

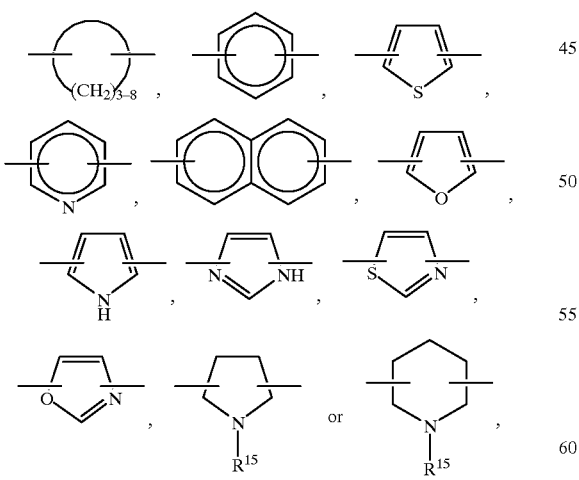

where $R^{15}$ is H, $C_1$–$C_8$ alkyl, $C_1$–$C_{20}$ alkycarbonyl, $C_1$–$C_{20}$ alkoxycarbonyl, or benzyl, or A together with $R^3$ and the nitrogen atom to which they are attached form a heterocyclic moiety of the formula:

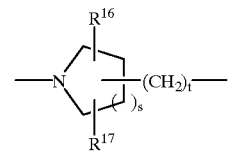

where s is 0, 1, 2, 3 or 4; t is 0 to 15; and $R^{16}$ and $R^{17}$ are, independently, hydrogen, $C_1$–$C_8$ alkyl, $C_1$–$C_8$ alkoxy, $C_1$–$C_8$ alkylcarbonyl, hydroxy, cyano, $C_1$–$C_8$ alkylcarbonyloxy, or —($CH_2$)$_{0-6}$—$NR^{18}R^{19}$; where $R^{19}$ is $C_1$–$C_8$ alkyl, $C_1$–$C_8$ alkoxycarbonyl, or $C_1$–$C_8$ alkylcarbonyl; and $R^{19}$ is hydrogen or $C_1$–$C_8$ alkyl;

$R^1$ and $R^2$ are independently hydrogen, $C_1$–$C_8$ alkyl, $C_1$–$C_8$ alkoxy, $C_1$–$C_8$ alkylcarbonyl, hydroxy, cyano, $C_1$–$C_8$ alkylcarbonyloxy, or —($CH_2$)$_{0-6}$—$NR^{18}R^{19}$; where $R^{18}$ is $C_1$–$C_8$ allyl, $C_1$–$C_8$ alkoxycarbonyl, or $C_1$–$C_8$ alkylcarbonyl; and $R^{19}$ is —H or $C_1$–$C_8$ alkyl;

$R^3$ is H, $C_1$–$C_8$ alkyl or $C_7$–$C_{15}$ arylalkyl where aryl is phenyl optionally substituted with a $C_1$–$C_6$ alkyl group; or $R^3$ is combined with A to form a heterocyclic ring as described above;

$R^4$ and $R^5$ are independently hydrogen, $C_1$–$C_{20}$ alkyl, $C_2$–$C_{20}$ alkenyl, $C_3$–$C_{10}$ cycloalkyl, cycloalkylalkyl having 3–10 carbon atoms in the cycloalkyl moiety and 1–20 carbon atoms in the alkyl moiety, —($CH_2$)$_{1-20}$—$Ar^1$, or —($CH_2$)$_{1-20}$—$NR^{20}R^{21}$; where $R^{20}$ is $C_1$–$C_{20}$ alkyl, $C_2$–$C_{20}$ alkenyl, $C_1$–$C_{20}$ alkylcarbonyl, $C_1$–$C_{20}$ alkoxycarbonyl or benzyl; and $R^{21}$ is hydrogen or $C_1$–$C_{20}$ alkyl; or $R^4$ and $R^5$ together with the nitrogen atom to which they are attached form a heterocyclic moiety of the formula:

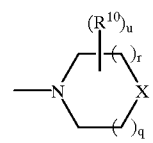

where q is 0, 1 or 2; r is 1 or 2; and u is 0, 1 or 2;

$R^{10}$ is $C_1$–$C_8$ alkyl; and

X is —O—, —S—, —$NR^{11}$— or —$CR^{12}R^{13}$— where $R^{11}$ is H, $C_1$–$C_{20}$ alkyl or benzyl;

$R^{12}$ is H, OH, $C_1$–$C_{20}$ alkyl, $C_1$–$CC_{20}$ alkoxy, $C_1$–$C_{20}$ alkylcarbonyloxy, $Ar^1$, or —($CH_2$)$_{1-10}$—$Ar^1$;

$R^{13}$ is H or $C_1$–$C_{20}$ alkyl; or $R^{12}$ and $R^{13}$ together with the carbon atom to which they are attached form a 3 to 8 membered carbocyclic ring;

or a pharmaceutically acceptable salt thereof.

14. A compound according to claim 12 having the formula:

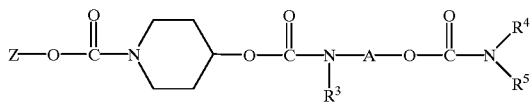

in which Z, $R^3$, $R^4$ and $R^5$ are as defined in claim 12 or a pharmaceutically acceptable salt thereof.

15. A compound according to claim 14 wherein Z is 4-phenoxyphenyl.

16. A compound according to claim 15 which is: 4-[6-(hexylcarbamoyloxy)hexylcarbamoyloxy]-piperidine-1-carboxylic acid 4-phenoxyphenyl ester.

17. A compound according to claim 15 which is: 4-[6-(dihexyl-carbamoyloxy)-hexylcarbamoyloxy]-piperidine-1-carboxylic acid 4-phenoxyphenyl ester.

18. A compound according to claim 15 which is: 4-[12-(hexylcarbamoyloxy)-dodecylcarbamoyloxy]-piperidine-1-carboxylic acid 4-phenoxyphenyl ester.

19. A compound according to claim 15 which is: (Z)-4-[6-(octadec-9-enylcarbamoyloxy)-hexylcarbamoyloxy]-piperidine-1-carboxylic acid 4-phenoxyphenyl ester.

20. A compound according to claim 15 which is: (Z)-4[12-(octadec-9-enylcarbamoyloxy)-dodecylcarbamoyloxy]-piperidine-1-carboxylic acid 4-phenoxyphenyl ester.

21. A compound according to claim 15 which is: 4-[3-(hexylcarbamoyloxy)-propylcarbamoyloxy]-piperidine-1-carboxylic acid 4-phenoxyphenyl ester.

22. A compound according to claim 15 which is: 4-[3-(nonylcarbamoyloxy)-propylcarbamoyloxy]-piperidine-1-carboxylic aid 4-phenoxyphenyl ester.

23. A method for reducing cholesterol absorption through the intestinal wall of a mammal which comprises internally administering thereto a therapeutically effective amount of a compound having the formula:

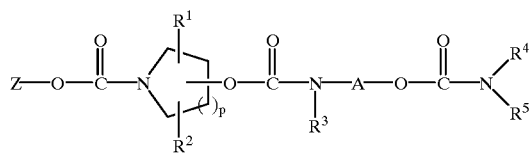

wherein
p is 2;
Z is $Ar^1$, $—Ar^1—Ar^2$, $—Ar^1—O—Ar^2$, or $—Ar^1—S—Ar^2$;
$Ar^1$ and $Ar^2$ are, independently, selected from phenyl and naphthyl;
$Ar^1$ and $Ar^2$, independently, are optionally substituted by fluorine, chlorine, bromine, iodine, cyano, nitro, $C_1$–$C_{20}$ alkyl, $C_2$–$C_{20}$ alkenyl, $C_3$–$C_8$ cycloalkyl, $C_1$–$C_{20}$ alkoxy, $C_1$–$C_{20}$ alkyl-O—($C_1$–$C_{20}$ alkyl)—, $C_1$–$C_{20}$ alkyl-O—($C_1$–$C_{20}$ -alkyl)—O—, trifluoromethyl, $C_1$–$C_{20}$ alkylcarbonyl, $C_3$–$C_8$ cycloalkyloxy, —OH, —SH, —$(CH_2)_{1-6}$—OH, —$NH_2$, or —$(CH_2)_{1-6}$—$NR^8R^9$; where
$R^8$ is $C_1$–$C_{20}$ alkyl, and
$R^9$ is hydrogen or $C_1$–$C_{20}$ alkyl;
A is a bridging group selected from a saturated or unsaturated, straight or branched hydrocarbon chain of 1 to 20 carbon atoms and which may have 1 to 6 sites of olefinic and/or acetylenic unsaturation;

$R^1$ and $R^2$ are independently hydrogen, $C_1$–$C_8$alkyl, $C_1$–$C_8$ alkoxy, $C_1$–$C_8$ alkylcarbonyl, hydroxy, or cyano;
$R^3$ is H, $C_1$–$C_8$ alkyl or $C_7$–$C_{15}$ arylalkyl where aryl is phenyl optionally substituted with a $C_1$–$C_6$ alkyl group;
$R^4$ and $R^5$ are independently hydrogen, $C_1$–$C_{20}$ alkyl, $C_2$–$C_{20}$ alkenyl, $C_3$–$C_{10}$ cycloalkyl, or cycloalkylalkyl having 3–10 carbon atoms in the cycloalkyl moiety and 1–20 carbon atoms in the alkyl moiety,
or a pharmaceutically acceptable salt thereof.

24. A pharmaceutical composition for decreasing cholesterol absorption in a mammal which comprises a pharmaceutically acceptable carrier and a therapeutically effective amount of a compound having the formula:

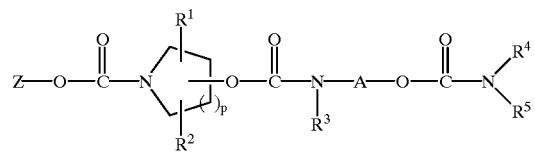

wherein
p is 2;
Z is $—Ar^1$, $—Ar^1—Ar^2$, $—Ar^1—O—Ar^2$, or $—Ar^1—S—Ar^2$;
$Ar^1$ and $Ar^2$ are, independently, selected from phenyl and naphthyl;
$Ar^1$ and $Ar^2$, independently, are optionally substituted by fluorine, chlorine, bromine, iodine, cyano, nitro, $C_1$–$C_{20}$ alkyl, $C_2$–$C_{20}$ alkenyl, $C_3$—$C_8$ cycloalkyl, $C_1$–$C_{20}$ alkoxy, $C_1$–$C_{20}$ alkyl-O—($C_1$–$C_{20}$ alkyl)—, $C_1$–$C_{20}$ alkyl-O—($C_1$–$C_{20}$-alkyl)—O—, trifluoromethyl, $C_1$–$C_{20}$ alkylcarbonyl, $C_3$–$C_8$ cycloalkyloxy, —OH, —SH, —$(CH_2)_{1-6}$—OH, —$NH_2$, or —$(CH_2)_{1-6}$—$NR^8R^9$; where
$R^8$ is $C_1$–$C_{20}$ alkyl, and
$R^9$ is hydrogen or $C_1$–$C_{20}$ alkyl;
A is a bridging group selected from a saturated or unsaturated, straight or branched hydrocarbon chain of 1 to 20 carbon atoms and which may have 1 to 6 sites of olefinic and/or acetylenic unsaturation;
$R^1$ and $R^2$ are independently hydrogen, $C_1$–$C_8$ alkoxy, $C_1$–$C_8$ alkylcarbonyl, hydroxy, or cyano;
$R^3$ is H, $C_1$–$C_8$ alkyl or $C_7$–$C_{15}$ arylalkyl where aryl is phenyl optionally substituted with a $C_1$–$C_6$ alkyl group;
$R^4$ and $R^5$ are independently hydrogen, $C_1$–$C_{20}$ alkyl, $C_2$–$C_{20}$ alkenyl, $C_3$–$C_{10}$ cycloalkyl, or cycloalkylalkyl having 3–10 carbon atoms in the cycloalkyl moiety and 1–20 carbon atoms in the alkyl moiety,
or a pharmaceutically acceptable salt thereof.

25. A pharmaceutical composition for decreasing cholesterol absorption in a mammal which comprises a pharmaceutically acceptable carrier and a therapeutically effective amount of a compound having the formula:

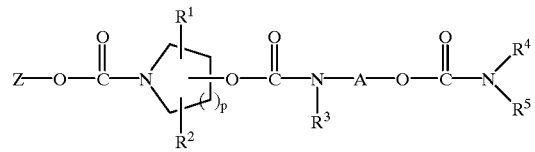

wherein
p is 0, 1, 2, 3, or 4;

Z is —Ar¹, —Ar¹—Ar², —Ar¹—O—Ar², —Ar¹—S—Ar²,

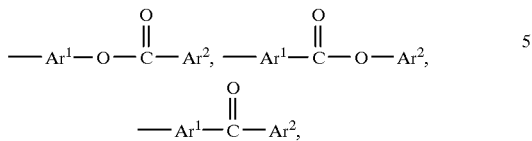

—Ar¹—(CH₂)₁₋₂₀—Ar², —Ar¹—(CH₂)₁₋₂₀—O—Ar², —Ar¹—O—(CH₂)₁₋₂₀—Ar², —Ar¹—(CR⁶=CR⁶)₁₋₃—Ar², or —Ar¹—NR⁷—Ar²; where R⁶ is hydrogen or $C_1-C_8$ alkyl; and R⁷ is hydrogen, $C_1-C_8$ alkyl, $C_1-C_8$ alkylcarbonyl, or $C_1-C_8$ alkoxycarbonyl; and Ar¹ and Ar² are, independently, selected from phenyl, naphthyl, indenyl, fluorenyl, furanyl, benzofuranyl, dibenzofuranyl, thienyl, benzothienyl, pyridinyl, indolyl, quinolinyl, isoquinolinyl, carbazolyl, pyrimidinyl, pyrazinyl, imidazolyl, benzimidazolyl, benzotriazolyl, oxazolyl, benzoxazolyl, isoxazolyl, benzisoxazolyl, or thiazolyl, benzthiazolyl; and Ar¹ and Ar², independently, are optionally substituted by fluorine, chlorine, bromine, iodine, cyano, nitro, —CO₂H, $C_1-C_{20}$ alkyl, $C_2-C_{20}$ alkenyl, $C_3-C_8$ cycloalkyl, $C_1-C_{20}$ alkoxy, $C_1-C_{20}$ alkyl-O—($C_1-C_{20}$ alkyl)—, $C_1-C_{20}$ alkyl-O—($C_1-C_{20}$-alkyl)—O—, trifluoromethyl, $C_1-C_{20}$ alkylcarbonyl, $C_3-C_8$ cycloalkyloxy, $C_1-C_{20}$ alkylcarbonyloxy, $C_1-C_{20}$ alkoxycarbonyl, mono or di $C_1-C_{20}$ alkylaminocarbonyl, tetrazolyl, —OH, —SH, —(CH₂)₁₋₆—OH, —NH₂, or —(CH₂)₁₋₆—NR⁸R⁹; where R⁸ is $C_1-C_{20}$ alkyl, $C_1-C_{20}$ alkylcarbonyl, $C_1-C_{20}$ alkoxycarbonyl; and R⁹ is hydrogen or $C_1-C_{20}$ alkyl; or R⁸ and R⁹ together with the nitrogen atom to which they are attached form a heterocyclic ring of the formula:

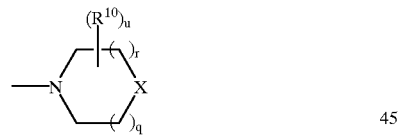

where q is 0, 1 or 2; r is 1 or 2; and u is 0, 1 or 2; R¹⁰ is $C_1-C_8$ alkyl; and X is —O—, —S—, —NR¹¹— or —CR¹²R¹³—; where R¹¹ is H, $C_1-C_{20}$ alkyl or benzyl;

R¹² is H, OH, $C_1-C_{20}$ alkyl, $C_1-C_{20}$ alkoxy, $C_1-C_{20}$ alkylcarbonyloxy, Ar¹, or —(CH₂)₁₋₁₀—Ar¹;

R¹³ is H or $C_1-C_{20}$ alkyl; or

R¹² and R¹³ together with the carbon atom to which they are attached form a 3 to 8 membered carbocyclic ring;

A is a bridging group selected from:
(1) a saturated or unsaturated, straight or branched hydrocarbon chain of 1 to 20 carbon atoms and which may have 1 to 6 sites of olefinic and/or acetylenic unsaturation;
(2) a group of the formula: —(CH₂)ₘ—W—(CH₂)ₙ—, where m and n are 1 to 19, m plus n is 2 to 20; and W is a group selected from —O—, —S— or —NR¹⁴—; where R¹⁴ is hydrogen, $C_1-C_{20}$ alkyl, $C_1-C_{20}$ alkylcarbonyl, $C_1-C_{20}$ alkoxycarbonyl or benzyl;

(3) a group of the formula:

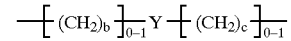

where b and c are, independently, 1 to 20, and b plus c is 1 to 20, and Y is selected from the group consisting of:

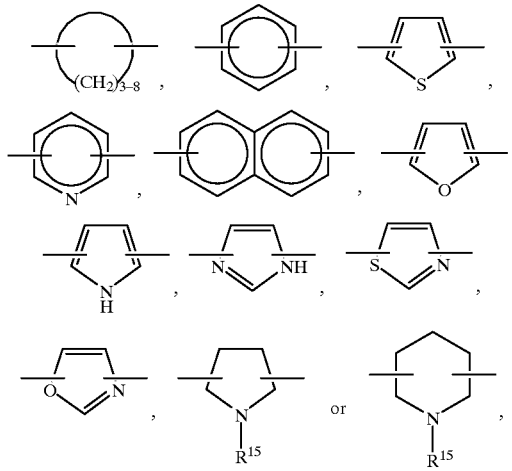

where R¹⁵ is H, $C_1-C_8$ alkyl, $C_1-C_{20}$ alkylcarbonyl, $C_1-C_{20}$ alkoxycarbonyl, or benzyl; or A together with R³ and the nitrogen atom to which they are attached form a heterocyclic moiety of the formula:

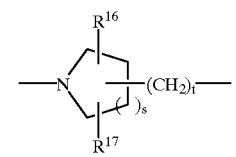

where s is 0, 1, 2, 3 or 4; t is 0 to 15; and R¹⁶ and R¹⁷ are, independently, hydrogen, $C_1-C_8$ alkyl, $C_1-C_8$ alkoxy, $C_1-C_8$ alkylcarbonyl, hydroxy, cyano, $C_1-C_8$ alkylcarbonyloxy, or —(CH₂)₀₋₆—NR¹⁸R¹⁹; where R¹⁸ is $C_1-C_8$ alkyl, $C_1-C_8$ alkoxycarbonyl, or $C_1-C_8$ alkylcarbonyl; and R¹⁹ is hydrogen or $C_1-C_8$ alkyl;

R¹ and R² are independently hydrogen, $C_1-C_8$ alkyl, $C_1-C_8$ alkoxy, $C_1-C_8$ alkylcarbonyl, hydroxy, cyano, $C_1-C_8$ alkylcarbonyloxy, or —(CH₂)₀₋₆—NR¹⁸R¹⁹; where R¹⁸ is $C_1-C_8$ alkyl, $C_1-C_8$ alkoxycarbonyl, or $C_1-C_8$ alkylcarbonyl; and R¹⁹ is —H or $C_1-C_8$ alkyl;

R³ is H, $C_1-C_8$ alkyl or $C_7-C_{15}$ arylalkyl where aryl is phenyl optionally substituted with a $C_1-C_6$ alkyl group; or R³ is combined with A to form a heterocyclic ring as described above;

R⁴ and R⁵ are independently hydrogen, $C_1-C_{20}$ alkyl, $C_2-C_{20}$ alkenyl, $C_3-C_{10}$ cycloalkyl, cycloalkylalkyl having 3–10 carbon atoms in the cycloalkyl moiety and 1–20 carbon atoms in the alkyl moiety, —(CH₂)₁₋₂₀Ar¹, or —(CH₂)₁₋₂₀NR²⁰R²¹; where R²⁰ is $C_1-C_{20}$ alkyl, $C_2-C_{20}$ alkenyl, $C_1-C_{20}$ alkylcarbonyl, $C_1-C_{20}$ alkoxycarbonyl or benzyl; and $R^{21}$ is hydrogen or $C_1$–$C_{20}$ alkyl; or $R^4$ and $R^5$ together with the nitrogen atom to which they are attached form a heterocyclic moiety of the formula:

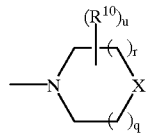

where r, q, u, $R^{10}$ and X are as defined above,
or a pharmaceutically acceptable salt thereof.

26. A method for reducing cholesterol absorption through the intestinal wall of a mammal which comprises internally administering thereto a therapeutically effective amount of a compound having the formula:

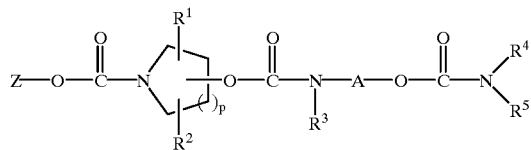

wherein p is 0, 1, 2, 3, or 4;

Z is —$Ar^1$, —$Ar^1$—$Ar^2$, —$Ar^1$—O—$Ar^2$, —$Ar^1$—S—$Ar^2$,

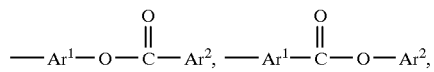

—$Ar^1$—$(CH_2)_{1-20}$—$Ar^2$, —$Ar^1$—$(CH_2)_{1-20}$—O—$Ar^2$, —$Ar^1$—O—$(CH_2)_{1-20}$—$Ar^2$, —$Ar^1$—$(CR^6=CR^6)_{1-3}$—$Ar^2$, or —$Ar^1$—$NR^7$—$Ar^2$; where $R^6$ is hydrogen or $C_1$–$C_8$ alkyl; and $R^7$ is hydrogen, $C_1$–$C_8$ alkyl, $C_1$–$C_8$ alkylcarbonyl, or $C_1$–$C_8$ alkoxycarbonyl; and $Ar^1$ and $Ar^2$ are, independently, selected from phenyl, naphthyl, indenyl, fluorenyl, furanyl, benzofuranyl, dibenzofuranyl, thienyl, benzothienyl, pyridinyl, indolyl, quinolinyl, isoquinolinyl, carbazolyl, pyrimidinyl, pyrazinyl, imidazolyl, benzimidazolyl, benzotriazolyl, oxazolyl, benzoxazolyl, isoxazolyl, benzisoxazolyl, or thiazolyl, benzthiazolyl; and $Ar^1$ and $Ar^2$, independently, are optionally substituted by fluorine, chlorine, bromine, iodine, cyano, nitro, —$CO_2H$, $C_1$–$C_{20}$ alkyl, $C_2$–$C_{20}$ alkenyl, $C_3$–$C_8$ cycloalkyl, $C_1$–$C_{20}$ alkoxy, $C_1$–$C_{20}$ alkyl-O—($C_1$–$C_{20}$ alkyl)—, $C_1$–$C_{20}$ alkyl-O—($C_1$–$C_{20}$ -alkyl)—O—, trifluoromethyl, $C_1$–$C_{20}$ alkylcarbonyl, $C_3$–$C_8$ cycloalkyloxy, $C_1$–$C_{20}$ alkylcarbonyloxy, $C_1$–$C_{20}$ alkoxycarbonyl, mono or di $C_1$–$C_{20}$ alkylaminocarbonyl, tetrazolyl, —OH, —SH, —$(CH_2)_{1-6}$—OH, —$NH_2$, or —$(CH_2)_{1-6}$—$NR^8R^9$; where $R^8$ is $C_1$–$C_{20}$ alkyl, $C_1$–$C_{20}$ alkylcarbonyl, $C_1$–$C_{20}$ alkoxycarbonyl; and $R^9$ is hydrogen or $C_1$–$C_{20}$ alkyl; or $R^8$ and $R^9$ together with the nitrogen atom to which they are attached form a heterocyclic ring of the formula:

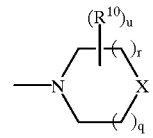

where q is 0, 1 or 2; r is 1 or 2; and u is 0, 1 or 2;

$R^{10}$ is $C_1$–$C_8$ alkyl; and

X is —O—, —S—, —$NR^{11}$— or —$CR^{12}R^{13}$—; where $R^{11}$ is H, $C_1$–$C_{20}$ alkyl or benzyl;

$R^{12}$ is H, OH, $C_1$–$C_{20}$ alkyl, $C_1$–$C_{20}$ alkoxy, $C_1$–$C_{20}$ alkylcarbonyloxy, $Ar^1$, or —$(CH_2)_{1-10}$—$Ar^1$;

$R^{13}$ is H or $C_1$–$C_{20}$ alkyl; or $R^{12}$ and $R^{13}$ together with the carbon atom to which they are attached form a 3 to 8 membered carbocyclic ring;

A is a bridging group selected from:
(1) a saturated or unsaturated, straight or branched hydrocarbon chain of 1 to 20 carbon atoms and which may have 1 to 6 sites of olefinic and/or acetylenic unsaturation;
(2) a group of the formula: —$(CH_2)_m$—W—$(CH_2)_n$—, where m and n are 1 to 19, m plus n is 2 to 20; and W is a group selected from —O—, —S— or —$NR^{14}$—; where $R^{14}$ is hydrogen, $C_1$–$C_{20}$ alkyl, $C_1$–$C_{20}$ alkylcarbonyl, $C_1$–$C_{20}$ alkoxycarbonyl or benzyl;
(3) a group of the formula:

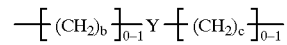

where b and c are, independently, 1 to 20, and b plus c is 1 to 20, and Y is selected from the group consisting of:

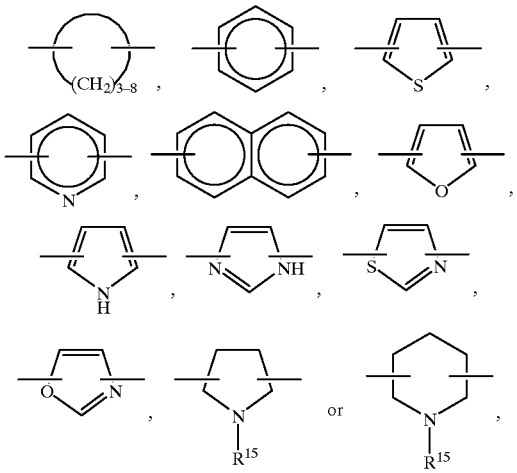

where $R^{15}$ is H, $C_1$–$C_8$ alkyl, $C_1$–$C_{20}$ alkylcarbonyl, $C_1$–$C_{20}$ alkoxycarbonyl, or benzyl; or A together with $R^3$ and the nitrogen atom to which they are attached form a heterocyclic moiety of the formula:

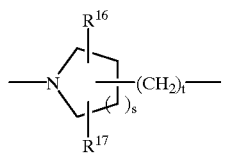

where s is 0, 1, 2, 3 or 4; t is 0 to 15; and $R^{16}$ and $R^{17}$ are, independently, hydrogen, $C_1$–$C_8$ alkyl, $C_1$–$C_8$ alkoxy, $C_1$–$C_8$ alkylcarbonyl, hydroxy, cyano, $C_1$–$C_8$ alkylcarbonyloxy, or —$(CH_2)_{0-6}$—$NR^{18}R^{19}$; where $R^{18}$ is $C_1$–$C_8$ alkyl, $C_1$–$C_8$ alkoxycarbonyl, or $C_1$–$C_8$ alkylcarbonyl; and $R^{19}$ is hydrogen or $C_1$–$C_8$ alkyl;

$R^1$ and $R^2$ are independently hydrogen, $C_1$–$C_8$ alkyl, $C_1$–$C_8$ alkoxy, $C_1$–$C_8$ alkylcarbonyl, hydroxy, cyano, $C_1$–$C_8$ alkylcarbonyloxy, or —$(CH_2)_{0-6}$—$NR^{18}R^{19}$; where R18 is $C_1$–$C_8$ alkyl, $C_1$–$C_8$ alkoxycarbonyl, or $C_1$–$C_8$ alkylcarbonyl; and $R^{19}$ is —H or $C_1$–$C_8$ alkyl;

$R^3$ is H, $C_1$–$C_8$ alkyl or $C_7$–$C_{15}$ arylalkyl where aryl is phenyl optionally substituted with a $C_1$–$C_6$ alkyl group; or $R^3$ is combined with A to form a heterocyclic ring as described above;

$R^4$ and $R^5$ are independently hydrogen, $C_1$–$C_{20}$ alkyl, $C_2$–$C_{20}$ alkenyl, $C_3$–$C_{10}$ cycloalkyl, cycloalkylalkyl having 3–10 carbon atoms in the cycloalkyl moiety and 1–20 carbon atoms in the alkyl moiety, —$(CH_2)_{1-20}Ar^1$, or —$(CH_2)_{1-20}NR^{20}R^{21}$; where $R^{20}$ is $C_1$–$C_{20}$ alkyl, $C_2$–$C_{20}$ alkenyl, $C_1$–$C_{20}$ alkylcarbonyl, $C_1$–$C_{20}$ alkoxycarbonyl or benzyl; and $R^{21}$ is hydrogen or $C_1$–$C_{20}$ alkyl; or $R^4$ and $R^5$ together with the nitrogen atom to which they are attached form a heterocyclic moiety of the formula:

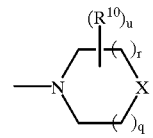

where r, q, u, $R^{10}$ and X are as defined above, or a pharmaceutically acceptable salt thereof.

27. A method according to claim 26 wherein the therapeutically effective compound is selected from a compound according to claim 8.

* * * * *